(12) United States Patent
Pendrak et al.

(10) Patent No.: US 7,504,243 B2
(45) Date of Patent: Mar. 17, 2009

(54) METHODS FOR THE PRODUCTION OF BILIVERDIN

(75) Inventors: Michael L. Pendrak, Kensington, MD (US); David D. Roberts, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 245 days.

(21) Appl. No.: 11/078,552

(22) Filed: Mar. 14, 2005

(65) Prior Publication Data

US 2005/0209305 A1 Sep. 22, 2005

Related U.S. Application Data

(60) Provisional application No. 60/554,369, filed on Mar. 19, 2004.

(51) Int. Cl.
*C12P 17/16* (2006.01)
*C07D 405/00* (2006.01)
*A01N 43/04* (2006.01)
*A61K 31/4025* (2006.01)
*A61K 31/70* (2006.01)

(52) U.S. Cl. .................. 435/118; 514/45; 514/422; 548/517

(58) Field of Classification Search .................. 435/118
See application file for complete search history.

(56) References Cited

U.S. PATENT DOCUMENTS

| | | | |
|---|---|---|---|
| 4,770,997 | A | 9/1988 | Yoshino |
| 4,985,360 | A | 1/1991 | Takahashi |
| 5,624,811 | A | 4/1997 | Lang |
| 2003/0027124 | A1 | 2/2003 | Maines |
| 2003/0162826 | A1 | 8/2003 | Clark |
| 2005/0214331 | A1 * | 9/2005 | Levy .......................... 424/400 |

FOREIGN PATENT DOCUMENTS

| | | |
|---|---|---|
| DE | 32 39 236 | 9/1983 |
| EP | 0 005 637 | 11/1979 |
| EP | 0 140 004 | 5/1985 |
| EP | 0 247 846 | 12/1987 |
| EP | 0 320 095 | 6/1989 |

OTHER PUBLICATIONS

Abraham, N. G. et al. (1988) "The physiological significance of heme oxygenase," Int. J. Biochem. 20:543-558.
Auclair, K. et al. (2003) "Cloning And Expression Of A Heme Binding Protein From The Genome Of *Saccharomyces cerevisiae*," Protein Expression Purif. 28:340-349.
Barañano D.E. et al. (2002) "Biliverdin Reductase: A Major Physiologic Cytoprotectant," Proc. Natl. Acad. Sci (USA) 99(25):16093-16098.
Bensen, E.S. et al. (2002) "A Forkhead Transcription Factor Is Important For True Hyphal As Well As Yeast Morphogenesis in *Candida albicans*," Eukaryot. Cell 1:787-798.
Beri, R. et al. (1993) Chemistry And Biology Of Heme. Effect Of . . . , Drug Metab Rev. 25(1-2):49-152.
Berman, J. et al. (2002) "*Candida albicans*: A Molecular Revolution Built On Lessons From Budding Yeast," Nat Rev Genet. 3(12):918-930.
Bratlid, D. (1991) "Bilirubin Toxicity: Pathophysiology And Assessment Of Risk Factors," N Y State J Med. 91(11):489-492.
Care, R.S. et al. (1999) "The MET3 Promoter: A New Tool For *Candida albicans* Molecular Genetics," Mol. Microbiol. 34:792-798.
Chaney, R. L. (1998) "Plants Can Utilize Iron From Iron-N, N'-di-2 Hydroxybenzoylethylenediamine-N, N'-Diacetic Acid . . . ," J. Plant Nutr. 11, 1033-1050.
Chiu, H. et al. (2002) "Differential Induction Of Heme Oxygenase-1 In Macrophages And Hepatocytes During . . . ," Toxicol Appl. Pharmacol. 181(2):106-115.
Colpaert, E. et al. (2002) "Investigation Of The Potential Modulatory Effect Of Biliverdin, Carbon Monoxide And . . . ," Eur. J. Pharmacol. 457(2-3):177-86.
Crapo, J.D. (2003) "Oxidative Stress As An Initiator Of Cytokine Release And Cell Damage," Eur Respir J Suppl. 44:4s-6s.
Cuzzocrea, S. et al. (2001) "Antioxidant Therapy: A New Pharmacological Approach In Shock, Inflammation, And . . . ," Pharmacol Rev. 53(1):135-159.
Datta, A. et al. (1989) "Current Trends In *Candida albicans* Research," Adv Microb Physiol. 30:53-88.
Djousse, L. et al. (2001) "Total Serum Bilirubin And Risk Of Cardiovascular Disease In The Framingham Offspring Study," Am. J. Cardiol. 87:1196-200.
Durante, W. (2003) "Heme Oxygenase-1 In Growth Control And Its Clinical Application To Vascular Disease," J. Cell. Physiol. 195, 373-382.
Elbirt, K.K. et al. (1999) "Heme Oxygenase: Recent Advances In Understanding Its Regulation And Role," Proc. Assoc. Am. Physicians 111:438-447.
Fondevila, C. (2003) "Biliverdin Protects Rat Livers From Ischemia/Reperfusion Injury," Transplant Proc. 35(5):1798-1799.
Fonzi, W.A. et al. (1993) "Isogenic Strain Construction and Gene Mapping in *Candida albicans*," Genetics 134:717-728.
Fujita, T. et al. (2001) "Paradoxical Rescue From Ischemic Lung Injury By Inhaled Carbon Monoxide Driven By Derepression Of Fibrinolysis," Nat. Med. 7:598-604.
Galbraith R. (1999) "Heme Oxygenase: Who Needs It?," Proc Soc Exp Biol Med. 222(3):299-305.

(Continued)

*Primary Examiner*—Herbert J. Lilling
(74) *Attorney, Agent, or Firm*—Berenato, White & Stavish

(57) ABSTRACT

The present invention relates to compositions and methods for the production of biliverdin. In particular, the invention concerns methods for producing biliverdin in yeast, especially *Candida albicans*, and other microorganisms.

11 Claims, 9 Drawing Sheets

OTHER PUBLICATIONS

Genco, C.A. et al. (2001) "Emerging Strategies In Microbial Haem Capture," Mol. Microbiol. 39:1-11.

Hampton, M.B. et al. (1998) "Inside The Neutrophil Phagosome: Oxidants, Myeloperoxidase, And Bacterial Killing," Blood 92:3007-3017.

Hansen, T. W. (2002) "Mechanisms Of Bilirubin Toxicity: Clinical Implications," Clin Perinatol. 29(4):765-778.

Heyman, E. et al. (1989) "Retinopathy Of Prematurity And Bilirubin," N. Engl. J. Med. 320:256.

Hidalgo, F.J. et al. (1990) "Can Serum Bilirubin Be An Index Of In Vivo Oxidative Stress?," Med Hypotheses 33(3):207-211.

Hopkins, P.N. et al. (1996) "Higher Serum Bilirubin Is Associated With Decreased Risk for Early Familial Coronary . . .," Arterioscler. Thromb. Vasc. Biol. 16:250-255.

Kato, Y. et al. (2003) "Bilirubin Rinse: A Simple Protectant Against The Rat Liver Graft Injury Mimicking Heme Oxygenase-1 Preconditioning," Hepatology 38:364-373.

Katori, M. et al. (2002) "A Novel Strategy Against Ischemia And Reperfusion Injury: Cytoprotection With Heme Oxygenase System," Transpl Immunol. 9(2-4):227-233.

Luo, G. et al. (2001) "Candida Species Exhibit Differential In Vitro Hemolytic Activities," J. Clin. Microbiol. 39, 2971-2974.

Manns, J.M. et al. (1994) "Production Of A Hemolytic Factor By *Candida albincans*," Infect. Immun. 62:5154-5156.

Machlin, L.J. et al. (1987) "Free Radical Tissue Damage: Protective Role Of Antioxidant Nutrients," FASEB J. 1(6):441-445.

Maines, M. D. (1988) "Heme Oxygenase: Function, Multiplicity, Regulatory Mechanisms, And Clinical Applications," FASEB J. 2:2557-2568.

Mantle, T. J. (2002) "Haem Degradation In Animals And Plants," Biochem Soc Trans. 30(4):630-633.

McDonagh, A.F. et al. (1980) "Preparation And Properties Of Crystalline Biliverdin IX Alpha. Simple Methods For Preparing Isomerically . . . ," Biochem. J. 189:193-208.

McGeary, R.P. et al. (2003) "Biological Properties And Therapeutic Potential Of Bilirubin," Mini Rev Med Chem. 3(3):253-256.

Montellano, P.R. (2000) "The Mechanism Of Heme Oxygenase," Curr Opin Chem Biol. 4(2):221-227.

Moore, M.R. (1980) "The Biochemistry Of The Porphyrins," Clin Haematol. 9(2):227-252.

Muramoto, T. et al. (2002) "Expression and Biochemical Properties of a Ferredoxin-Dependent Heme Oxygenase Required for . . . ," Plant Physiol. 130, 1958-1966.

Nakagami, T. et al. (1992) "Antiviral Activity Of A Bile Pigment, Biliverdin, Against Human Herpesvirus 6 (HHV-6) In Vitro," Microbiol Immunol 36(4):381-390.

O'Carra, P. et al. (1969) "Haem Catabolism And Coupled Oxidation Of Haemproteins," FEBS Lett. 5:295-298.

Ogawa, K. (2002) "Heme Metabolism In Stress Response," Nippon Eiseigaku Zasshi 56(4):615-21.

Otterbein, L.E. (2003) "Heme Oxygenase-1: Unleashing The Protective Properties Of Heme," Trends. Immunol. 24:449-455.

Pendrak, M.L. et al. (2000) "Structural Requirements For Hemoglobin To Induce Fibronectin Receptor Expression In *Candida albicans*," Biochemistry 39:16110-16118.

Pendrak, M.L. et al. (2004) "Heme Oxygenase in *Candida albicans* Is Regulated by Hemoglobin and Is Necessary for Metabolism o," J. Biol. Chem. 279(5):3426-3433.

Philpott, C.C. et al. (1998) "Cell-Cycle Arrest And Inhibition Of G1 Cyclin Translation By Iron In AFT1-1up Yeast," EMBO J. 17, 5026-5036.

Philpott, C.C. et al. (2002) "The Response To Iron Deprivation In *Saccharomyces cerevisiae*: Expression Of Siderophore-Based . . . ," Biochem. Soc. Trans. 30:698-702.

Protchenko, O. et al. (2003) "Regulation Of Intracellular Heme Levels By HMX1, A Homologue Of Heme Oxygenase, In . . . ," J. Biol. Chem. 278:36582-36587.

Reggiori, F. et al. (2001) "Sorting Of Proteins Into Multivesicular Bodies: Ubiquitin-Dependent And -Independent Targeting," EMBO J. 20:5176-5186.

Rodrigues, R.G. et al. (1998) "Hemoglobin Differentially Induces Binding Of Candida, Trichosporon, And Saccharomyces Species To Fibronectin," J. Infect. Dis. 178:497-502.

Ryter, S.W. et al. (2000) "The Heme Synthesis And Degradation Pathways: Role In Oxidant Sensitivity. Heme Oxygenase Has Both . . . ," Free Radic Biol Med 28(2):289-309.

Saito, S. et al. (1982) "Verdohemochrome IX Alpha: Preparation And Oxidoreductive Cleavage To Biliverdin IX Alpha," Proc. Natl. Acad. Sci. U. S. A. 79, 1393-1397.

Sano, S. et al. (1986) "On The Mechanism Of The Chemical And Enzymic Oxygenations Of Alpha-Oxyprotohemin IX To . . . ," Proc. Natl. Acad. Sci. U. S. A. 83:531-535.

Santos, R. et al. (2003) "Haemin Uptake And Use As An Iron Source By *Candida albicans*: Role Of CaHMX1-Encoded Haem Oxygenase," Microbiology 149:579-588.

Schacter, B.A. (1988) "Heme Catabolism By Heme Oxygenase: Physiology, Regulation, And Mechanism Of Action," Semin. Hematol. 25:349-369.

Schmitt, M.P. (1997) "Utilization Of Host Iron Sources By Corynebacterium Diphtheriae: Identification Of A Gene Whose Product Is . . . ," J. Bacteriol. 179:838-845.

Schuller, D.J. et al. (1999) "Crystal Structure Of Human Heme Oxygenase-1," Nat. Struct. Biol. 6:860-867.

Schwertner, H.A. et al. (1994) "Association Of Low Serum Concentration Of Bilirubin With Increased Risk Of Coronary Artery Disease," Clin. Chem. 40:18-23.

Shibahara, S. et al. (2002) "Heme Degradation And Human Disease: Diversity Is The Soul Of Life," Antioxid Redox Signal. 4(4):593-602.

Sikka, S.C. (2001) "Relative Impact Of Oxidative Stress On Male Reproductive Function," Curr Med Chem. 8(7):851-62.

Srikantha, T. et al. (1995) "The Frequency Of Integrative Transformation At Phase-Specific Genes Of *Candida albicans* Correlates With . . . ," Mol. Gen. Genet. 246:342-352.

Srikantha, T. et al. (1996) "The Sea Pansy Renilla reniformis Luciferase Serves As A Sensitive Bioluminescent Reporter For Differential Gene Expression in *Candida albicans*," J.

Stocker, R. et al. (1987) "Antioxidant Activity Of Albumin-Bound Bilirubin," Proc. Natl. Acad. Sci. USA 84:5918-5922.

Stojiljkovic, I. et al. (2002) "Processing Of Heme And Heme-Containing Proteins By Bacteria," DNA Cell Biol. 21:281-295.

Sun, J. et al. (1994) "Identification Of Histidine 25 As The Heme Ligand In Human Liver Heme Oxygenase," Biochemistry 33:13734-13740.

Temme, E.H. et al. "Serum Bilirubin And 10-Year Mortality Risk In A Belgian Population," (2001) Cancer Causes Control 12:887-894.

Vitek, L. et al. (2002) "Gilbert Syndrome And Ischemic Heart Disease: A Protective Effect Of Elevated Bilirubin Levels," Atherosclerosis 160:449-456.

Wang, H.D. et al. (2002) "Bilirubin Ameliorates Bleomycin-Induced Pulmonary Fibrosis In Rats," Am J Respir Crit Care Med. 165(3):406-411.

Weinberg, E.D. (1999) "The Role Of Iron In Protozoan And Fungal Infectious Diseases," J. Eukaryot. Microbol. 46:231-238.

Weissman, Z. et al. (2002) "Deletion Of The Copper Transporter CaCCC2 Reveals Two Distinct Pathways For Iron Acquisition In *Candida albicans*," Mol. Microbiol. 44, 1551-1560.

Wennberg, R. P. (1991) "Cellular Basis Of Bilirubin Toxicity," N Y State J Med. 91(11):493-496.

Wilks, A. (2002) "Heme Oxygenase: Evolution, Structure, And Mechanism," Antioxid. Redox Signal. 4(4):603-614.

Wilson, R. et al. (1999) "Rapid Hypothesis Testing with *Candida albicans* through Gene Disruption with Short Homology Regions," J. Bacteriol. 181:1868-1874.

Yamaguchi-Iwai, Y. et al. (1996) "Iron-Regulated DNA Binding By The AFT1 Protein Controls The Iron Regulon In Yeast," EMBO J. 15, 3377-3384.

Yamamoto, T. (1968) "Synthesis Of Bilirubin," Naika Hokan. 15(11):391-398.

Yan, S. et al. (1996) "Specific Induction Of Fibronectin Binding Activity By Hemoglobin In *Candida albicans* Grown In . . . ," Infect. Immun. 64:2930-2935.

Yoshida, T. et al. (2000) "Mechanism Of Heme Degradation By Heme Oxygenase," J. Inorg. Biochem. 82(1-4):33-41.

Zhang, L. et al. (1994) "The Yeast Activator HAP1—A GAL4 Family Member—Binds DNA In A Directly Repeated Orientation," Genes Dev. 8:2110-2119.

Zhu, W. et al. (2000) "Use Of Heme Compounds As Iron Sources By Pathogenic Neisseriae Requires The Product Of The HemO Gene," J. Bacteriol. 182, 439-447.

Stocker, R. et al. (1987) "Bilirubin Is An Antioxidant of Possible Physiological Importance," Science 235, 1043-1046.

* cited by examiner

Figure 3
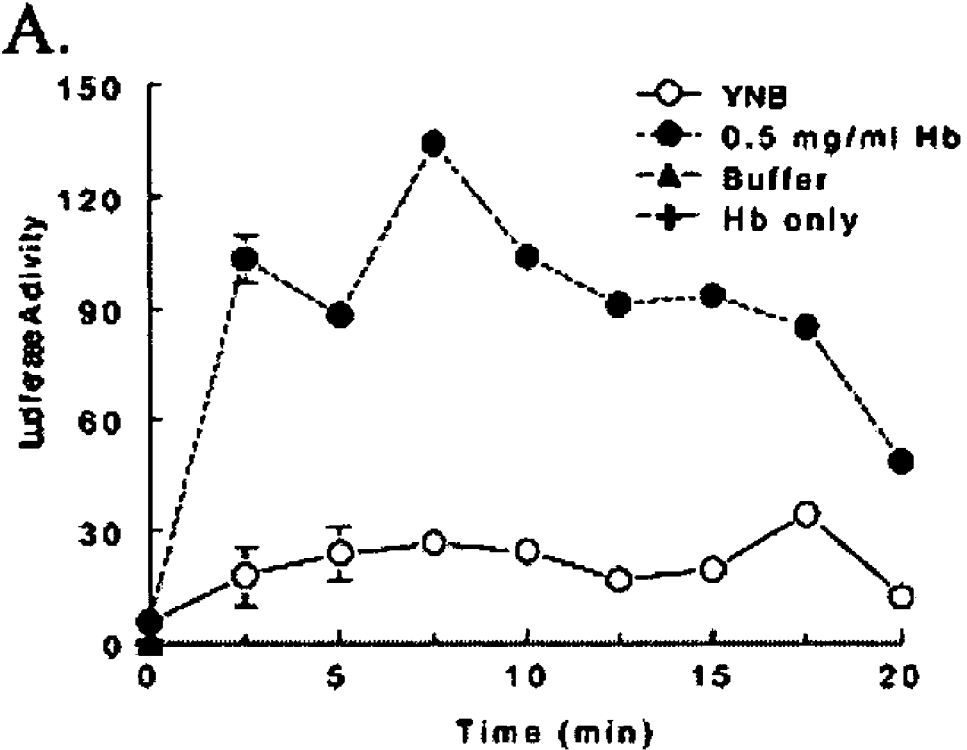
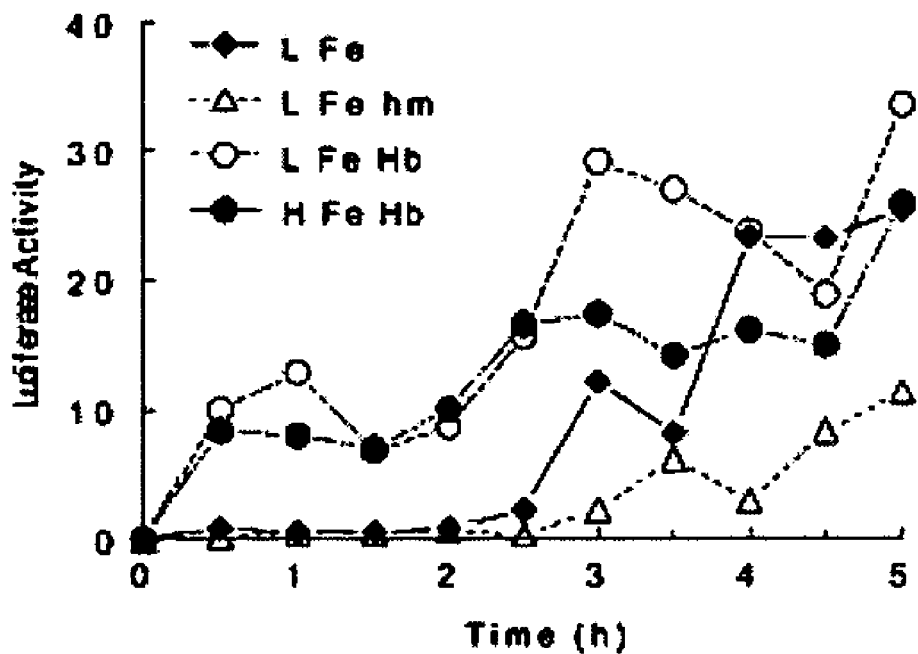

Figure 6

```
Ca  MQYKSSGATSKLSQVEIIPAKTDVGALANRINLETRSLHDRADKTVTLKF  50
          .|      .    |.   :    |:  .| .|:         .|
Hu  ..............MERPQPDSMPQDLSEALKEATKEVHTQAENA...EP  33
                          ↑ ↑   ● ●              ●

51  ALALRNYKVYRQG....LQAFYHVFASIEKALYRQLEKKDEWSEMLEQVW  96
      . | | |    :  . ||::  .:|.    ::|:  | |  .    |:
34  MRNFQKGQVTRDGFKLVMASLYHIYVALEE....EIERNKE.SPVFAPVY  78
    ● ●                       ▽

97  KP.EIARAGKAEQDLLFFYDDNKEKFIKPIMPAQIEFCKHILEVTEEKPY  145
    | |: |   |||| |.|      :. | |  ||   : | : ||    .|
79  FPEELHRKAALEQDLAFWYGPRWQEVI.PYTPAMQRYVKRLHEVGRTEPE  127
                                          ▽

146 LLFAYLHVMYLALFAGGRIMRSSVLKATGMYPQRDGLSHDDVVRMGTNFF  195
    || |: :  ||  .||.:::    ||   :   :||.           ||
128 LLVAHAYTRYLGDLSGGQVLKKIAQKALDLPSSGEGLA..........FF  167
          ▽↑▲ ▽     ▲

196 TF.DVPDEDLLRLTYKRDYELVTRNGLTEEQKLEIIEESKYIFEHDVKCV  244
    || .:      : |:   .   :|   :  :|||.|  |   .:.
168 TFPNIASATKFKQLYRSRMNSLE...MTPAVRQRVIEEAKTAFLLNIQLF  214
              ↑  ↑                          ● ▽    ●

245 AELEK...HNMDKLSGTWTYFLVTRGYYAALVLFSLLALIYLRRVVNKLT  291
    ||:.    |.   |.     | |   .|  | | | :    |       |
215 EELQELLTHDTKDQSPSRAPGLRQRA..SNKVQDS..APVETPRGKPPLN  260
```

METHODS FOR THE PRODUCTION OF BILIVERDIN

CROSS-REFERENCE TO RELATED APPLICATIONS

This application claims a right of priority to U.S. Patent Application Ser. No. 60/554,369, filed Mar. 19, 2004, which application is hereby incorporated by reference in its entirety.

STATEMENT OF GOVERNMENTAL INTEREST

This invention was funded by National Cancer Institute of the National Institutes of Health of the United States of America. The United States Government has certain rights to this invention.

FIELD OF THE INVENTION

The present invention relates to compositions and methods for the production of biliverdin. In particular, the invention concerns methods for producing biliverdin in yeast, especially *Candida albicans*, and other microorganisms.

BACKGROUND OF THE INVENTION

Oxidative stress plays a critical role in the development of vascular disease (Barañano D. E. et al. (2002) "BILIVERDIN REDUCTASE: A MAJOR PHYSIOLOGIC CYTOPROTECTANT," Proc. Natl. Acad. Sci (USA) 99(25):16093-16098). Cells use multiple systems to protect against reactive oxygen species. The concentration of free heavy metals, which can catalyze the formation of free radicals, are tightly regulated by chelators such as ferritin and transferrin. Enzymes with antioxidant actions include catalase and superoxide dismutase, which together convert superoxide radicals into water. Small molecules, such as ascorbate and α-tocopherol act as direct antioxidants, quenching the propagation of free radicals. Glutathione occurs at millimolar concentrations in most tissues and is generally regarded as the principal endogenous intracellular small molecule antioxidant cytoprotectant.

Bilirubin is a lipophilic linear tetrapyrrole that occurs uniquely in mammals, and is abundant in plasma (Beri, R. et al. (1993) "CHEMISTRY AND BIOLOGY OF HEME. EFFECT OF METAL SALTS, ORGANOMETALS, AND METALLOPORPHYRINS ON HEME SYNTHESIS AND CATABOLISM, WITH SPECIAL REFERENCE TO CLINICAL IMPLICATIONS AND INTERACTIONS WITH CYTOCHROME P-450," Drug Metab Rev. 25(1-2):49-152; Yamamoto, T. (1968) "SYNTHESIS OF BILIRUBIN," Naika Hokan. 15(11):391-398; Moore, M. R. (1980) "THE BIOCHEMISTRY OF THE PORPHYRINS," Clin Haematol. 9(2):227-252). In humans, approximately 250-400 mg of bilirubin are formed daily as the final metabolic product of heme catabolism, as heme oxygenase (HO) cleaves the heme ring to form biliverdin (Yoshida, T. et al. (2000) "MECHANISM OF HEME DEGRADATION BY HEME OXYGENASE," J. Inorg. Biochem. 82(1-4):33-41; Montellano, P. R. (2000) "THE MECHANISM OF HEME OXYGENASE," Curr Opin Chem Biol. 4(2):221-227; Galbraith R. (1999) "HEME OXYGENASE: WHO NEEDS IT?," Proc Soc Exp Biol Med. 222(3):299-305), which is then reduced by biliverdin reductase (BVR) to yield bilirubin (Wilks, A. (2002) "HEME OXYGENASE: EVOLUTION, STRUCTURE, AND MECHANISM," Antioxid. Redox Signal. 4(4):603-614; Mantle, T. J. (2002) "HAEM DEGRADATION IN ANIMALS AND PLANTS," Biochem Soc Trans. 30(4):630-633; Ogawa, K. (2002) "HEME METABOLISM IN STRESS RESPONSE," Nippon Eiseigaku Zasshi 56(4):615-21). Approximately 80% of serum bilirubin is derived from hemoglobin of senescent erythrocytes that have been phagocytized by macrophages in the reticuloendothelial system (Shibahara, S. et al. (2002) "HEME DEGRADATION AND HUMAN DISEASE: DIVERSITY IS THE SOUL OF LIFE," Antioxid Redox Signal. 4(4):593-602); the remainder derives from the catabolism of other haemoproteins and from the destruction of maturing red blood cells in the marrow.

Bilirubin has been found to possesses strong antioxidant potential against peroxyl and other reactive oxygen radicals (McGeary, R. P. et al. (2003) "BIOLOGICAL PROPERTIES AND THERAPEUTIC POTENTIAL OF BILIRUBIN," Mini Rev Med Chem. 3(3):253-256; Stocker, R. et al. (1987) "BILIRUBIN IS AN ANTIOXIDANT OF POSSIBLE PHYSIOLOGICAL IMPORTANCE," Science 235, 1043-1046; Hidalgo, F. J. et al. (1990) "CAN SERUM BILIRUBIN BE AN INDEX OF IN VIVO OXIDATIVE STRESS?," Med Hypotheses 33(3):207-211; Stocker, R. et al. (1987) "ANTIOXIDANT ACTIVITY OF ALBUMIN-BOUND BILIRUBIN," Proc. Natl. Acad. Sci. USA 84:5918-5922; Machlin, L. J. et al. (1987) "FREE RADICAL TISSUE DAMAGE: PROTECTIVE ROLE OF ANTIOXIDANT NUTRIENTS," FASEB J. 1(6):441-445; Otterbein, L. E. et al. (2003) "HEME OXYGENASE-1: UNLEASHING THE PROTECTIVE PROPERTIES OF HEME," Trends Immunol. 24(8):449-455; Wang, H. D. et al. (2002) "BILIRUBIN AMELIORATES BLEOMYCIN-INDUCED PULMONARY FIBROSIS IN RATS," Am J Respir Crit Care Med. 165(3):406-411).

Several epidemiological studies have found that bilirubin levels are inversely associated with coronary artery disease and mortality from myocardial infarction (Scriver, C. R. (1995) "THE METABOLIC AND MOLECULAR BASES OF INHERITED DISEASE," (McGraw-Hill, New York; Vitek, L. et al. (2002) "GILBERT SYNDROME AND ISCHEMIC HEART DISEASE: A PROTECTIVE EFFECT OF ELEVATED BILIRUBIN LEVELS," Atherosclerosis 160: 449-456; Schwertner, H. A. et al. (1994) "ASSOCIATION OF LOW SERUM CONCENTRATION OF BILIRUBIN WITH INCREASED RISK OF CORONARY ARTERY DISEASE," Clin. Chem. 40:18-23; Hopkins, P. N. et al. (1996) "HIGHER SERUM BILIRUBIN IS ASSOCIATED WITH DECREASED RISK FOR EARLY FAMILIAL CORONARY ARTERY DISEASE," Arterioscler. Thromb. Vasc. Biol. 16:250-255; Djousse, L. et al. (2001) "TOTAL SERUM BILIRUBIN AND RISK OF CARDIOVASCULAR DISEASE IN THE FRAMINGHAM OFFSPRING STUDY," Am. J. Cardiol. 87:1196-200; Heyman, E. et al. (1989) "RETINOPATHY OF PREMATURITY AND BILIRUBIN," N. Engl. J. Med. 320: 256; Temme, E. H. et al. "SERUM BILIRUBIN AND 10-YEAR MORTALITY RISK IN A BELGIAN POPULATION," (2001) Cancer Causes Control 12:887-894).

The possibility that the administration of bilirubin might find utility in providing cytoprotection is, however, encumbered by the toxicity and insolubility of the molecule (Hansen, T. W. (2002) "MECHANISMS OF BILIRUBIN TOXICITY: CLINICAL IMPLICATIONS," Clin Perinatol. 29(4):765-778; Wennberg, R. P. (1991) "CELLULAR BASIS OF BILIRUBIN TOXICITY," NY State J Med. 91(11):493-496; Bratlid, D. (1991) "BILIRUBIN TOXICITY: PATHOPHYSIOLOGY AND ASSESSMENT OF RISK FACTORS," N Y State J Med. 91(11):489-492). Excessive elevations of bilirubin lead to substantial deposits in the brain with the resultant kernicterus causing major brain damage (Barañano D. E. et al. (2002) "BILIVERDIN REDUCTASE: A MAJOR PHYSIOLOGIC CYTOPROTECTANT," Proc. Natl. Acad. Sci (USA) 99(25): 16093-16098; Orth, J. (1875) Virchows Arch. Pathol. Anat. 63, 447-462).

In contrast to bilirubin, biliverdin is soluble. It can be produced by incubating bilirubin in the presence of a bilirubin oxidase (E.C.1.3.3.5). A number of enzymes with bilirubin oxidase activity from various plant sources are known (See, U.S. Pat. Nos. 5,624,811; 4,985,360 and 4,770,997, European Patent Documents Nos. EP 0 140 004; EP 0 247 846; EP 0 005 637 and EP 0 320 095, and German Patent Document No. DE 32 39 236).

Biliverdin has been proposed to be potentially useful as a cytoprotective therapeutic agent (Barañano D. E. et al. (2002) "BILIVERDIN REDUCTASE: A MAJOR PHYSIOLOGIC CYTOPROTECTANT," Proc. Natl. Acad. Sci (USA) 99(25):16093-16098; Colpaert, E. et al. (2002) "INVESTIGATION OF THE POTENTIAL MODULATORY EFFECT OF BILIVERDIN, CARBON MONOXIDE AND BILIRUBIN ON NITRERGIC NEUROTRANSMISSION IN THE PIG GASTRIC FUNDUS," Eur. J. Pharmacol. 457(2-3):177-86; Nakagami, T. et al. (1992) "ANTIVIRAL ACTIVITY OF A BILE PIGMENT, BILIVERDIN, AGAINST HUMAN HERPESVIRUS 6 (HHV-6) IN VITRO," Microbiol Immunol 36(4):381-390; Katori, M. et al. (2002) "A NOVEL STRATEGY AGAINST ISCHEMIA AND REPERFUSION INJURY: CYTOPROTECTION WITH HEME OXYGENASE SYSTEM," Transpl Immunol. 9(2-4):227-233; Ryter, S. W. et al. (2000) "THE HEME SYNTHESIS AND DEGRADATION PATHWAYS: ROLE IN OXIDANT SENSITIVITY. HEME OXYGENASE HAS BOTH PRO- AND ANTIOXIDANT PROPERTIES," Free Radic Biol Med 28(2):289-309; U.S. Patent Application Publication No. 20030162826).

In particular, biliverdin has been proposed to be useful to treat vasoconstriction (U.S. Patent Application Publication No. 20030027124), coronary artery disease (Vitek, L. et al. (2002) "GILBERT SYNDROME AND ISCHEMIC HEART DISEASE: A PROTECTIVE EFFECT OF ELEVATED BILIRUBIN LEVELS," Atherosclerosis 160:449-456; Schwertner, H. A. et al. (1994) "ASSOCIATION OF LOW SERUM CONCENTRATION OF BILIRUBIN WITH INCREASED RISK OF CORONARY ARTERY DISEASE," Clin. Chem. 40:18-23; Hopkins, P. N. et al. (1996) "HIGHER SERUM BILIRUBIN IS ASSOCIATED WITH DECREASED RISK FOR EARLY FAMILIAL CORONARY ARTERY DISEASE," Arterioscler. Thromb. Vasc. Biol. 16:250-255; Djousse, L. et al. (2001) "TOTAL SERUM BILIRUBIN AND RISK OF CARDIOVASCULAR DISEASE IN THE FRAMINGHAM OFFSPRING STUDY," Am. J. Cardiol. 87:1196-200; Heyman, E. et al. (1989) "RETINOPATHY OF PREMATURITY AND BILIRUBIN," N. Engl. J. Med. 320: 256; Temme, E. H. et al. "SERUM BILIRUBIN AND 10-YEAR MORTALITY RISK IN A BELGIAN POPULATION," (2001) Cancer Causes Control 12:887-894) and ischemia/reperftision injury (Fondevila, C. (2003) "BILIVERDIN PROTECTS RAT LIVERS FROM ISCHEMIA/REPERFUSION INJURY," Transplant Proc. 35(5):1798-1799). Biliverdin has been found to block acetaminophen-induced injury (Chiu, H. et al. (2002) "DIFFERENTIAL INDUCTION OF HEME OXYGENASE-1 IN MACROPHAGES AND HEPATOCYTES DURING ACETAMINOPHEN-INDUCED HEPATOTOXICITY IN THE RAT: EFFECTS OF HEMIN AND BILIVERDIN," Toxicol Appl. Pharmacol. 181(2):106-115), and liver graft injury (Kato, Y. et al. (2003) "BILIRUBIN RINSE: A SIMPLE PROTECTANT AGAINST THE RAT LIVER GRAFT INJURY MIMICKING HEME OXYGENASE-1 PRECONDITIONING," Hepatology 38:364-373).

Despite improved methods of producing biliverdin, a need continues to exist for efficient and inexpensive methods for producing biliverdin, and in particular, methods capable of producing a single biliverdin isomer. The present invention is directed to such needs.

SUMMARY OF THE INVENTION

The present invention relates to compositions and methods for the production of biliverdin. In particular, the invention concerns methods for producing biliverdin in yeast, especially *Candida albicans*, and other microorganisms.

In one aspect, the invention relates to a method for producing biliverdin, wherein said method comprises the steps of: (A) culturing a microorganism in the presence of a heme compound, wherein said microorganism possesses a heme oxygenase activity sufficient to convert heme into biliverdin; and (B) recovering the produced biliverdin.

In another aspect, the invention relates to a biliverdin composition produced by the process of: (A) culturing a microorganism in the presence of a heme compound, wherein said microorganism possesses a heme oxygenase activity sufficient to convert heme into biliverdin; and (B) recovering the produced biliverdin.

In another aspect, the invention relates to a pharmaceutical composition comprising an amount of biliverdin sufficient to treat a disease or condition in a human or non-human mammal, or in tissue therefrom, wherein said disease or condition is selected from the group consisting of cancer, cardiovascular disease, inflammation and Alzheimer's disease, and wherein said biliverdin is produced by the process of: (A) culturing a microorganism in the presence of a heme compound, wherein said microorganism possesses a heme oxygenase activity sufficient to convert heme into biliverdin; and (B) recovering the produced biliverdin.

In another aspect, the invention relates to a method of treating a human or non-human. mammal for a disease or condition selected from the group consisting of cancer, cardiovascular disease, inflammation and Alzheimer's disease, wherein said method comprises administering to said human or non-human mammal a pharmaceutical composition comprising an amount of biliverdin sufficient to treat said disease or condition, wherein said biliverdin is produced by the process of: (A) culturing a microorganism in the presence of a heme compound, wherein said microorganism possesses a heme oxygenase activity sufficient to convert heme into biliverdin; and (B) recovering the produced biliverdin.

BRIEF DESCRIPTION OF THE FIGURES

FIG. 3 illustrates that CaHMX1 transcription is rapidly activated by hemoglobin. Panel A, activation of the CaHMX1 promoter by hemoglobin. *Renilla* luciferase activity from the 1.4-kb CaHMX1 promoter transcriptional fusion using knock-in strain Ki-29. Cells are cultured in YNB media with or without 25 μM Hb. Equivalent cell numbers are harvested at the indicated times, and extracts are analyzed for luciferase activity. Activity is defined as light units/cell number ±S.D. using identical lysis and assay volumes. The light levels of 25 μM Hb or assay buffer alone in the volume used for cell extracts in the presence of luciferase substrate are insignificant (shown at time zero). Panel B, activation of CaHMX1 transcription by Hb occurs in the presence and absence of iron. Ki-29 cells are cultured for 24 h in iron-deficient medium (L Fe) with the following additions: 25 μM hemin (LFehm), 25 μM Hb (LFeHb), 1.2 μM FeCl$_3$, and 25 μM Hb (HFeHb). Equivalent cell numbers are harvested at the indicated times and assayed for light production.

FIG. 6 demonstrates the identification of a heme oxygenase protein signature in CaHmx1p. The hypothetical translation of the CaHMX1 coding region (top) is shown aligned with *Homo sapiens* oxygenase isoform-1 (bottom). Alignment was carried out using GAP (http://molbio.info.nih.gov/molbio/molbio_docs/gcg/gap.html) (Needleman, S. B. et al. (1970) "A GENERAL METHOD APPLICABLE TO THE SEARCH FOR SIMILARITIES IN THE AMINO ACID SEQUENCE OF TWO PROTEINS," J. Mol. Biol. 48:443-453). Identification of essential catalytic residues as listed was made from the crystal structure of human heme oxygenase-1 (Schuller, D. J. et al. (1999) "CRYSTAL STRUCTURE OF HUMAN HEME OXYGENASE-1," Nat. Struct. Biol. 6:860-867). Filled ovals, direct heme contacts of proximal helix; filled triangles, residues unique to heme oxygenases contained within a highly conserved region (bar); filled circles, α meso-edge hydrophobic contacts; arrows, interactions with heme propionate residues at γ meso-edge; inverted open triangles, polar residues involved in ligand discrimination.

DESCRIPTION OF THE PREFERRED EMBODIMENTS

The present invention derives in part from the recognition that bilirubin is a potentially important cytoprotectant for organ transplant, coronary artery disease, and cancer treatment. The invention recognizes that owing to the toxicity and side-effects inherent in administering bilirubin, the bilirubin precursor, biliverdin, is a preferred therapeutic agent for administration to humans and non-human mammals (especially bovine, equine, porcine, ovine, canine, feline, and simian animals) in the treatment of organ rejection, coronary artery disease, and cancer.

Figure 1:
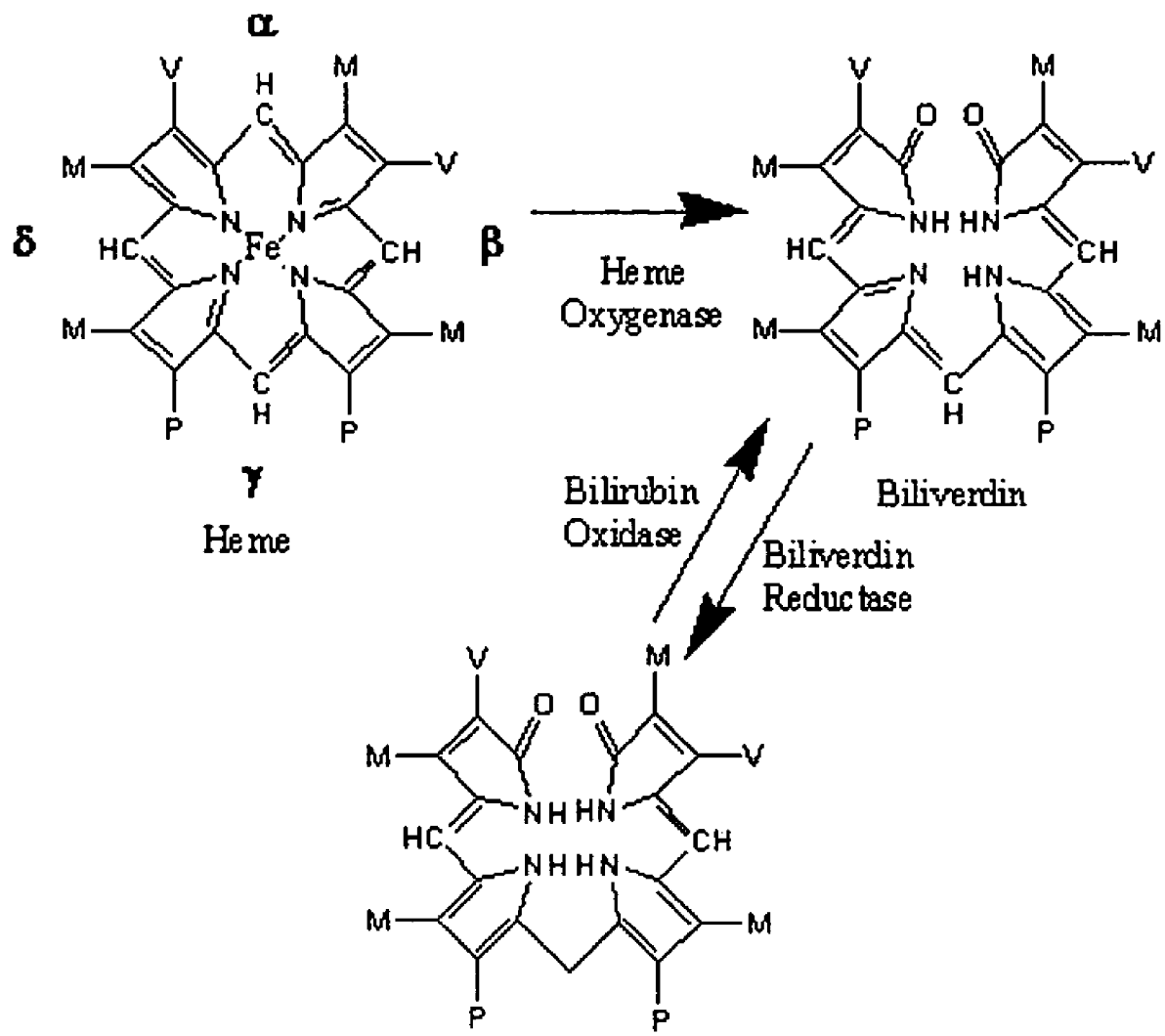
FIG. 1 shows the metabolism of heme into biliverdin and bilirubin. The Greek letters indicate the four meso-edge positions susceptible to oxidative modifications. Heme oxygenases cleave at the α meso-edge of heme to form α-biliverdin, whereas chemical oxidations of heme yield all four isomers. M, methyl, V, vinyl; P, propionic acid.

As indicated above, heme metabolism typically involves the conversion of heme to biliverdin in a reaction catalyzed by heme oxygenase. The produced biliverdin is then converted to bilirubin through the action of biliverdin reductase (FIG. 1). Current methods to produce biliverdin require relatively scarce starting materials, or require the use of biliverdin oxidase to convert bilirubin back into biliverdin (see, e.g., U.S. Pat. No. 5,624,811). Some current methods produce a mixture of isomers, only one of which is active.

Mammalian heme oxygenases are essential for normal heme protein turnover in the body and are directly responsible for recycling of Hb iron from normal turnover of senescent red cells or release because of trauma (Elbirt, K. K. et al. (1999) "HEME OXYGENASE: RECENT ADVANCES IN UNDERSTANDING ITS REGULATION AND ROLE," Proc. Assoc. Am. Physicians 111: 438-447). Heme oxygenase catalyzes the oxidative cleavage of the α meso-edge of heme. The reaction utilizes NADPH-reducing equivalents and a reductase to yield the open chain tetrapyrrole-biliverdin, CO, and iron (Abraham, N. G. et al. (1988) "THE PHYSIOLOGICAL SIGNIFICANCE OF HEME OXYGENASE," Int; J. Biochem. 20:543-558; Maines, M. D. (1988) "HEME OXYGENASE: FUNCTION, MULTIPLICITY, REGULATORY MECHANISMS, AND CLINICAL APPLICATIONS," FASEB J. 2:2557-2568; Schacter, B. A. (1988) "HEME CATABOLISM BY HEME OXYGENASE: PHYSIOLOGY, REGULATION, AND MECHANISM OF ACTION," Semin. Hematol. 25:349-369). Both CO and -biliverdin have cytoprotective activities (Durante, W. (2003) "HEME OXYGENASE-1 IN GROWTH CONTROL AND ITS CLINICAL APPLICATION TO VASCULAR DISEASE," J. Cell. Physiol. 195, 373-382; Otterbein, L. E. (2003) "HEME OXYGENASE-1: UNLEASHING THE PROTECTIVE PROPERTIES OF HEME," Trends. Immunol. 24:449-455).

Heme oxygenases have also been identified in plants and several bacteria including *Corynebacterium diphtheriae* (HmuO) (Schmitt, M. P. (1997) "UTILIZATION OF HOST IRON SOURCES BY *CORYNEBACTERIUM DIPHTHERIAE*: IDENTIFICATION OF A GENE WHOSE PRODUCT IS HOMOLOGOUS TO EUKARYOTIC HEME OXYGENASES AND IS REQUIRED FOR ACQUISITION OF IRON FROM HEME AND HEMOGLOBIN," J. Bacteriol. 179:838-845) and *Neisseria meningitidis* (HemO); Zhu, W. et al. (2000) "USE OF HEME COMPOUNDS AS IRON SOURCES BY PATHOGENIC NEISSERIAE REQUIRES THE PRODUCT OF THE HEMO GENE," J. Bacteriol. 182, 439-447). Null mutants of bacterial heme oxygenase (Schmitt, M. P. (1997) "UTILIZATION OF HOST IRON SOURCES BY *CORYNEBACTERIUM DIPHTHERIAE*: IDENTIFICATION OF A GENE WHOSE PRODUCT IS HOMOLOGOUS TO EUKARYOTIC HEME OXYGENASES AND IS REQUIRED FOR ACQUISITION OF IRON FROM HEME AND HEMOGLOBIN," J. Bacteriol. 179:838-845; Zhu, W. et al. (2000) "USE OF HEME COMPOUNDS AS IRON SOURCES BY PATHOGENIC NEISSERIAE REQUIRES THE PRODUCT OF THE HEMO GENE," J. Bacteriol. 182, 439-447) as well as the CaHMX1 of *C. albicans* (Santos, R. et al. (2003) "HAEMIN UPTAKE AND USE AS AN IRON SOURCE BY *CANDIDA ALBICANS*: ROLE OF CAHMX1-ENCODED HAEM OXYGENASE," Microbiology 149:579-588) have shown that a major role for microbial heme oxygenase is in the release of nutritional iron from heme and heme-protein complexes. *Saccharomyces cerevisiae* also expresses a protein containing the heme oxygenase protein signature (Reggiori, F. et al. (2001) "SORTING OF PROTEINS INTO MULTIVESICULAR BODIES: UBIQUITIN-DEPENDENT AND -INDEPENDENT TARGETING," EMBO J. 20:5176-5186; Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278:36582-36587), but direct enzymatic activity could not be demonstrated (Auclair, K. et al. (2003) "CLONING AND EXPRESSION OF A HEME BINDING PROTEIN FROM THE GENOME OF *SACCHAROMYCES CEREVISIAE*," Protein Expression Purif. 28:340-349). However, HMX1 is transcribed under conditions of iron deprivation, and its deletion leads to defects in iron accumulation and an increase in the intracellular heme pool (Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278:36582-36587).

The invention derives in part from the recognition that microorganisms that lack a biliverdin reductase, and thus naturally terminate their heme catabolism with the production of biliverdin, are preferred hosts for the production of biliverdin. The present invention thus provides an efficient method to produce the active isomer of biliverdin using the abundant starting material heme or heme-containing proteins, such as hemoglobin, by fermentation using such "biliverdin reductatase deficient" microorganisms. As used herein, a "biliverdin reductatase deficient" microorganism is a microorganism (including a mammalian cell, non-mammalian eukaryotic cell (especially yeast and fungal cells) and a bacterial cell), that lacks or substantially lacks a biliverdin reductase activity, such that the accumulated end-product of heme metabolism in such microorganism is biliverdin.

In one embodiment, such biliverdin reductatase deficient microorganisms will be microorganisms that have been mutated in either the bilirubin reductase gene or in one or more of its regulatory element(s) that diminishes the level or rate of gene expression of the endogenous biliverdin reductase, or which results in an endogenous biliverdin reductase having lower specific activity. As used herein, an diminished activity is one that is at least 50% less, and more preferably 200% less, still more preferably 500% less, than that exhibited prior to such diminution.

Such mutations can be in either the structural gene that encodes biliverdin reductase activity, in genes that encode inducers or repressors of such gene, or in regulatory sequences that control the extent or occurrence of biliverdin reductase expression. Methods for mutagenizing eukaryotic cells that can be adapted to produce such biliverdin reductatase deficient microorganisms are disclosed by Berman, J. et al. (2002) "*CANDIDA ALBICANS*: A MOLECULAR REVOLUTION BUILT ON LESSONS FROM BUDDING YEAST," Nat Rev Genet. 3(12):918-930, Datta, A. et al. (1989) "CURRENT TRENDS IN *CANDIDA ALBICANS* RESEARCH," Adv Microb Physiol. 30:53-88, Kumar, A. et al. (2001) "EMERGING TECHNOLOGIES IN YEAST GENOMICS," Nat Rev Genet. 2(4):302-12, Vidan, S. et al. (2001) "LARGE-SCALE MUTAGENESIS: YEAST GENETICS IN THE GENOME ERA," Curr Opin Biotechnol. 12(1):28-34, Spencer, J. F. et al. (1996) "MUTAGENESIS IN YEAST," Methods Mol Biol. 53:17-38, Theiss, S. et al. (2002) "NEW MOLECULAR METHODS TO STUDY GENE FUNCTIONS IN *CANDIDA* INFECTIONS," Mycoses 45(9-10):345-350, Venkatesan, R. N. et al. (2003) "SELECTION OF NOVEL EUKARYOTIC DNA POLYMERASES BY MUTAGENESIS AND GENETIC COMPLEMENTATION OF YEAST," Methods Mol Biol. 230: 19-26, Joshi, B. et al. (2002) "YEAST "KNOCKOUT-AND-RESCUE" SYSTEM FOR IDENTIFICATION OF eIF4E-FAMILY MEMBERS POSSESSING eIF4E-ACTIVITY," Biotechniques. 2002 August; 33(2):392-3, 395-396, 398 passim, Ross-Macdonald, P. (2000) "FUNCTIONAL ANALYSIS OF THE YEAST GENOME," Funct Integr Genomics. 1(2):99-113, Nadin-Davis, S. A. et al. (1998) "SITE-DIRECTED MUTAGENESIS OF LARGE PLASMIDS," Biotechniques. 25(6):1014-1019, Shuman, H. A. et al. (2003) "THE ART AND DESIGN OF GENETIC SCREENS: *ESCHERICHIA COLI*," Nat Rev Genet. 2003 June; 4(6):419-431, Braman, J. (2001) "IN VITRO MUTAGENESIS PROTOCOLS" In: Methods in Molecular Biology Vol. 182 (Humana Press, NY), Moore, M. M. et al. (1987) Banbury Reports 28: Mammalian Cell Mutagenesis," (Cold Spring Harbor Press, Cold Spring Harbor, N.Y.), and the like.

In a preferred embodiment, such biliverdin reductatase deficient microorganisms will be microorganisms that naturally lack a biliverdin reductatase activity. The yeast *Candida albicans* is such a microorganism. In accordance with the methods of the present invention, the use of *Candida albicans* to produce biliverdin is particularly preferred.

*Candida albicans* is an opportunistic pathogen that has adapted uniquely to its niche in the human host (Odds, F. C. (1988) "*CANDIDA* AND CANDIDOSIS," 2nd Ed., Bailliere Tindall, London). It is a commensal organism in the normal gastrointestinal flora, but becomes pathogenic following immunosuppressive chemotherapies for cancer, organ transplantation, and in AIDS patients (Groll, A. H., and Walsh, T. J. (2001) "UNCOMMON OPPORTUNISTIC FUNGI: NEW NOSOCOMIAL THREATS," Clin. Microbiol. Infect. 7:8-24). The switch from commensal colonization to invasive infection requires the exchange of specific signals between the pathogen and its host to allow survival and growth and to promote invasion of specific host tissues (Odds, F. C. (1988) "*CANDIDA* AND CANDIDOSIS," 2nd Ed., Bailliere Tindall, London). *Candida albicans* possesses a heme oxygenase which efficiently converts heme into biliverdin (see, Pendrak, M. L. et al. (2004) "HEME OXYGENASE IN CANDIDA ALBICANS IS REGULATED BY HEMOGLOBIN AND IS NECESSARY FOR METABOLISM OF EXOGENOUS HEME AND HEMOGLOBIN TO a-BILIVERDIN," J. Biol. Chem., Vol. 279, Issue 5, 3426-3433 (Originally published In Press as doi: 10.1074/jbc.M311550200 on Nov. 13, 2003).

The present invention discloses that hemoglobin (Hb) is one such host signal, based, in part, upon the observation that Hb is a specific inducer of a high affinity fibronectin receptor (Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118; Yan, S. et al. (1996) "SPECIFIC INDUCTION OF FIBRONECTIN BINDING ACTIVITY BY HEMOGLOBIN IN CANDIDA ALBICANS GROWN IN DEFINED MEDIA," Infect. Immun. 64:2930-2935). This induction was specific for Hb in that other host proteins or ferroproteins were inactive. Intact Hb was required for this activity because globin or hemin did not induce the fibronectin receptor (Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118). However, substitution of cobalt protoporphyrin IX ("CoPPIX") for the heme in globin restored activity, but coordination of CO, CN, and O2 as heme-axial ligands did not affect the activity of Hb (Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118). Hb bound saturably to the surface of Candida cells, which could be quantitatively inhibited by the Hb-binding protein haptoglobin (Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118). Signaling through the Hb receptor was independent of cellular iron status, because the fibronectin receptor was induced under conditions of iron sufficiency and preceded any detectable uptake of radioactive iron from Hb (Pendrak, M. L. et al. (2000) "STRUCTURAL REQUIREMENTS FOR HEMOGLOBIN TO INDUCE FIBRONECTIN RECEPTOR expression IN CANDIDA ALBICANS," Biochemistry 39:16110-16118). Together these data indicate that, although heme iron can be utilized by the fungus after prolonged culture (Santos, R. et al. (2003) "HAEMIN UPTAKE AND USE AS AN IRON SOURCE BY CANDIDA ALBICANS: ROLE OF CAHMX1-ENCODED HAEM OXYGENASE," Microbiology 149: 579-588), Hb signaling through the cell surface Hb receptor is rapid and independent of iron acquisition from the protein.

Because sensing of Hb may help the cells to recognize specific host tissue compartments, the gene regulation by Hb was investigated to gain insight into the fungal cellular functions that depend upon this signaling pathway. A differential display was employed to identify genes specifically regulated by Hb but not by inorganic iron. This analysis identified a C. albicans heme oxygenase gene (CaHMX1) that was shown recently to be regulated by iron and necessary for the organism to survive with heme as the sole iron source (Santos, R. et al. (2003) "HAEMIN UPTAKE AND USE AS AN IRON SOURCE BY CANDIDA ALBICANS: ROLE OF CAHMX1-ENCODED HAEM OXYGENASE," Microbiology 149:579-588).

The present invention demonstrates the transcriptional regulation of CaHMX1 by mammalian Hb and shows that this activation is iron-independent. CaHMX1 activation occurs rapidly following exposure to Hb and is additive with activation by iron deficiency. The present invention additionally shows that the CaHMX1 gene encodes a functional heme oxygenase enzyme and that the product of the reaction is α-biliverdin. In accordance with the methods of the present invention, α-biliverdin can therefore be readily produced by culturing C. albicans cells that possess the C. albicans heme oxygenase gene (CaHMX1 gene) in the presence of heme.

The invention also relates to the use of cells (including mammalian cells, yeast and other microorganisms) that possess an enhanced heme oxygenase activity, and to the use of such microorganisms in the production of biliverdin. As used herein, an enhanced activity is one that is at least 50% greater, and more preferably 200% greater, still more preferably 500% greater, than that exhibited prior to such enhancement. In accordance with such embodiments, the employed cells will possess one or more modifications that enhances either the specific activity of the heme oxygenase gene or affects one or more of its regulatory element(s) so as to enhance the level or rate of gene expression of the endogenous heme oxygenase activity.

In one embodiment, such enhanced microorganisms can be produced using the above-mentioned methods of cellular mutagenesis. In an alternate embodiment, suitable expression vectors can be used to clone and overexpress either an exogenous or heterologous heme oxygenase gene in a microorganism, especially a biliverdin reductase deficient microorganism. Examples of suitable vector systems and methods for employing them are known (see, e.g., Gao, Y. et al. (2002) "ADVANCES IN EUKARYOTIC EXPRESSION SYSTEMS," Zhonghua Nan Ke Xue. 8(4):292-4, 298; Brown W R et al. (2000) "ARTIFICIAL CHROMOSOMES: IDEAL VECTORS?" Trends Biotechnol. 8(5):218-23; Giga-Hama Y. et al. (1999) "EXPRESSION SYSTEM FOR FOREIGN GENES USING THE FISSION YEAST SCHIZOSACCHAROMYCES POMBE," Biotechnol Appl Biochem. 30(Pt 3):235-44; Kwon-Chung K J et al. (1998) "FATE OF TRANSFORMING DNA IN PATHOGENIC FUNGI," Med Mycol 36 Suppl 1:38-44; Bai C. et al. (1996) "GENE IDENTIFICATION USING THE YEAST TWO-HYBRID SYSTEM," Methods Enzymol. 1996; 273:331-47; Pompon, D. et al. (1995) "GENETICALLY ENGINEERED YEAST CELLS AND THEIR APPLICATIONS," Toxicol Lett. 82-83:815-22; Hensing, M. C. et al. (1995) "PHYSIOLOGICAL AND TECHNOLOGICAL ASPECTS OF LARGE-SCALE HETEROLOGOUS-PROTEIN PRODUCTION WITH YEASTS," Antonie Van Leeuwenhoek. 67(3):261-79; Hinnen, A. et al. (1995) "GENE EXPRESSION IN RECOMBINANT YEAST," Bioprocess Technol. 22:121-193; Jakobovits A. (1994) "YAC VECTORS. HUMANIZING THE MOUSE GENOME," Curr Biol. 4(8): 761-763; Bussineau, C. M. et al. (1994) "GENETIC STABILITY OF PROTEIN EXPRESSION SYSTEMS IN YEAST," Dev Biol Stand. 83:13-19; Gellissen, G. et al. (1992) "HETEROLOGOUS PROTEIN PRODUCTION IN YEAST," Antonie Van Leeuwenhoek. 2(1-2):79-93; Romanos, M. A. et al. (1992) "FOREIGN GENE EXPRESSION IN YEAST: A REVIEW," Yeast. 8(6):423-488; Aruffo, A. (1991) "EXPRESSION CLONING SYSTEMS," Curr Opin Biotechnol. 2(5): 735-741; Presutti, C. et al. (1991) "EXPRESSION VECTORS AND GENE TRANSFER," Ann Ist Super Sanita. 27(1):105-114; Russell, C. et al. (1991) "PRODUCTION OF RECOMBINANT PRODUCTS IN YEASTS: A REVIEW," Aust J Biotechnol. 5(1):48-55; Kurtz, M. B. et al. (1988) "The molecular genetics of Candida albicans," Microbiol Sci. 5(2):58-63; Kingsman, A. J. et al. (1987) "THE EXPRESSION OF HOMOLOGOUS AND HETEROLOGOUS GENES IN YEAST," Antonie Van Leeuwenhoek. 1987; 53(5): 325-333); Ghosh, S. et al. (2002) "BACULOVIRUS AS MAMMALIAN CELL EXPRESSION VECTOR FOR GENE THERAPY: AN EMERGING STRATEGY," Mol Ther. 6(1):5-11; Anton, G. (1994) "RETROVIRAL VECTORS," Rev Roum Virol. 45(3-4):193-202; Presutti, C. et al. (1991) "EXPRESSION VECTORS AND GENE TRANSFER," Ann Ist Super Sanita. 27(1):105-14; Miller, L. K. (1989) "INSECT BACULOVIRUSES: POWERFUL GENE EXPRESSION VECTORS," Bioessays. 1989 October; 11(4):91-95; Bendig, M. M. (1988) "THE PRODUCTION OF FOREIGN PROTEINS IN MAMMALIAN CELLS," Genet Eng. (7):91-127; Hruby, D. E. et al. (1987) "USE OF VACCINIA VIRUS TO EXPRESS BIOPHARMACEUTICAL PRODUCTS," Pharm Res. 4(2):92-97).

In one embodiment, such enhanced microorganisms can be produced using microorganisms endogenous heme oxygenase gene has been inactivated (see Examples below). Such a microorganism can be employed to either facilitate the cloning of functional heme oxygenase gene (e.g., via phenotypic complementation) or as strains that can be subjected to "reverse" Mutagenesis to obtain progeny strains that have recovered heme oxygenase activity. Mutants exhibiting enhanced heme oxygenase activity can be recovered from such progeny.

Uses of Biliverdin

The present invention relates to the use of biliverdin and its derivatives and therapeutically acceptable salts to provide cytoprotective therapy for a wide range of diseases and conditions, including inflammation, shock, coronary artery disease, cancer, tissue disease, tissue damage (e.g., damage to harvested organs, etc.), Alzheimer's disease, and other disorders and conditions. Indeed, a vast amount of evidence implicates reactive oxygen species as mediators of inflammation, shock, ischemia/reperfusion injury (Cuzzocrea, S. et al. (2001) "ANTIOXIDANT THERAPY: A NEW PHARMACOLOGICAL APPROACH IN SHOCK, INFLAMMATION, AND ISCHEMIA/REPERFUSION INJURY," Pharmacol Rev. 53(1):135-159; Crapo, J. D. (2003) "OXIDATIVE STRESS AS AN INITIATOR OF CYTOKINE RELEASE AND CELL DAMAGE," Eur Respir J Suppl. 44:4s-6s) and sterility (Sikka, S. C. (2001) "RELATIVE IMPACT OF OXIDATIVE STRESS ON MALE REPRODUCTIVE FUNCTION," Curr Med Chem. 8(7):851-62). Such reactive oxygen species are the targets of administered biliverdin compounds of the present invention, and the compositions of the present invention can be used to treat all such diseases and conditions.

The present invention also relates to the use of biliverdin and its derivatives and therapeutically acceptable salts to provide cytoprotective therapy to individuals suffering from, or at risk of suffering from, inflammation. The term "inflammation," as used herein, is meant to include reactions of the specific and non-specific defense systems. As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases, delayed type hypersensitivity response mediated by T-cells (as seen, for example in individuals who test "positive" in the Mantaux test), etc. A "non-specific defense system reaction" is a response mediated by leukocytes incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: asthma; adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity. The role of reactive oxygen in the etiology and pathology of inflammation has been described (see, e.g., Agostini, M. et al. (2002) "OXIDATIVE STRESS AND APOPTOSIS IN IMMUNE DISEASES," Int J Immunopathol Pharmacol. 15(3):157-164; Andreadis, A. A. et al. (2003) "OXIDATIVE AND NITROSATIVE EVENTS IN ASTHMA," Free Radic Biol Med. 35(3):213-25; Bowler, R. P. et al. (2002) "OXIDATIVE STRESS IN ALLERGIC RESPIRATORY DISEASES," J Allergy Clin Immunol. 110(3):349-56; Erichsen, K. et al. (2003) "FERROUS FUMARATE DETERIORATED PLASMA ANTIOXIDANT STATUS IN PATIENTS WITH CROHN DISEASE," Scand J Gastroenterol. 2003 May; 38(5):543-8; Hageman, G. J. et al. (2003) "SYSTEMIC POLY(ADP-RIBOSE) POLYMERASE-1 ACTIVATION, CHRONIC INFLAMMATION, AND OXIDATIVE STRESS IN COPD PATIENTS," Free Radic Biol Med. 35(2):140-8; Jialal, I. et al. (2002) "OXIDATIVE STRESS, INFLAMMATION, AND DIABETIC VASCULOPATHIES: THE ROLE OF ALPHA TOCOPHEROL THERAPY," Free Radic Res. 2002 December; 36(12):1331-1336; Kinnula, V. L. et al. (2003) "SUPEROXIDE DISMUTASES IN THE LUNG AND HUMAN LUNG DISEASES," Am J Respir Crit Care Med. 167(12):1600-19; Kumagai, S. et al. (2003) "PATHOLOGICAL ROLES OF OXIDATIVE STRESS IN AUTOIMMUNE DISEASES," Rinsho Byori. 51(2):126-32; Lang, J. D. et al. (2002) "OXIDANT-ANTIOXIDANT BALANCE IN ACUTE LUNG INJURY," Chest 122(6 Suppl):314S-320S; Langen, R. C. et al. (2003) "ROS IN THE LOCAL AND SYSTEMIC PATHOGENESIS OF [CHRONIC OBSTRUCTIVE PULMONARY DISEASE] COPD," Free Radic Biol Med. 2003 Aug. 1; 35(3):226-35; Liu, Y. et al. (2003) "BILIRUBIN AS A POTENT ANTIOXIDANT SUPPRESSES EXPERIMENTAL AUTOIMMUNE ENCEPHALOMYELITIS: IMPLICATIONS FOR THE ROLE OF OXIDATIVE STRESS IN THE DEVELOPMENT OF MULTIPLE SCLEROSIS," J Neuroimmunol. 139(1-2):27-35; Maier, C. M. et al. (2002) "ROLE OF SUPEROXIDE DISMUTASES IN OXIDATIVE DAMAGE AND NEURODEGENERATIVE DISORDERS," Neuroscientist. 8(4):323-34; Oh, T. Y. et al. (2001) "OXIDATIVE DAMAGES ARE CRITICAL IN PATHOGENESIS OF REFLUX ESOPHAGITIS: IMPLICATION OF ANTIOXIDANTS IN ITS TREATMENT," Free Radic Biol Med. 2001 Apr. 15; 30(8):905-15; Nadeem, A. et al. (2003) "INCREASED OXIDATIVE STRESS AND ALTERED LEVELS OF ANTIOXIDANTS IN ASTHMA," J Allergy Clin Immunol. 111(1):72-8; Osanai, K. (2003) "IMPLICATION OF OXIDANT STRESS IN AIRWAY INFLAMMATION," Nippon Rinsho. 61(12):2119-25; Pleiner, J. et al. (2003) "INFLAMMATION-INDUCED VASOCONSTRICTOR HYPOREACTIVITY IS CAUSED BY OXIDATIVE STRESS," J Am Coll Cardiol. 42(9):1656-62; Himmelfarb, J. et al. (2003) "OXIDATIVE STRESS IN UREMIA," Curr Opin Nephrol Hypertens. 12(6):593-8; Rahman, I. (2002) "Oxidative stress and gene transcription in asthma and chronic obstructive pulmonary disease: antioxidant therapeutic targets," Curr Drug Targets Inflamm Allergy. 1(3):291-315; Rahman, I. (2003) "OXIDATIVE STRESS, CHROMATIN REMODELING AND GENE TRANSCRIPTION IN INFLAMMATION AND CHRONIC LUNG DISEASES," J Biochem Mol Biol. 36(1):95-109; Selzner, N. et al. (20030 "PROTECTIVE STRATEGIES AGAINST ISCHEMIC INJURY OF THE LIVER," Gastroenterology. 125(3):917-36).

The present invention also relates to the use of biliverdin and its derivatives and therapeutically acceptable salts to provide cytoprotective therapy to individuals suffering from, or at risk of suffering from, cardiovascular disease. The role of reactive oxygen in the etiology and pathology of cardiovascular disease has been described (see, e.g., Alexander R W. (2003) "THE JEREMIAH METZGER LECTURE. PATHOGENESIS OF ATHEROSCLEROSIS: REDOX AS A UNIFYING MECHANISM," Trans Am Clin Climatol Assoc. 114:273-304; Chade, A. R. et al. (2004) "COMPARISON OF ACUTE AND CHRONIC ANTIOXIDANT INTERVENTIONS IN EXPERIMENTAL RENOVASCULAR DISEASE," Am J Physiol Renal Physiol. [E-published, http://ajprenal.physiology.org/ cgi/reprint/00385.2003v1]; Farquhar, M. J. et al. (2003) "OXIDATIVE STRESS AND THE MYELODYSPLASTIC SYNDROMES," Int J Hematol. 77(4):342-50; Kaysen, G. A. et al. (2004) "THE ROLE OF OXIDATIVE STRESS-ALTERED LIPOPROTEIN STRUCTURE AND FUNCTION AND MICROINFLAMMATION ON CARDIOVASCULAR RISK IN PATIENTS WITH MINOR RENAL DYSFUNCTION," J Am Soc Nephrol. 15(3):538-548; Matkovics A. (2003) "ANTIOXIDANTS AND VASCULAR DISEASES," Orv Hetil. 144(10):475-81; Nedeljkovic, Z. S. et al. (2003) "MECHANISMS OF OXIDATIVE STRESS AND VASCULAR DYSFUNCTION," Postgrad Med J. 79(930):195-199; quiz 198-200; Sanchez-Moreno, C. et al. (2004) "Decreased Levels Of Plasma Vitamin C And Increased Concentrations Of Inflammatory And Oxidative Stress Markers After Stroke," Stroke. 35(1):163-8. Epub 2003 Dec. 11; Tardif, J. C. et al. (2002) "PREVENTION OF RESTENOSIS WITH ANTIOXIDANTS: MECHANISMS AND IMPLICATIONS," Am J Cardiovasc Drugs. 2(5):323-34).

The present invention also relates to the use of biliverdin and its derivatives and therapeutically acceptable salts to provide cytoprotective therapy to individuals suffering from, or at risk of suffering from, cancer. The role of reactive oxygen in the etiology and pathology of cancer has been described (see, e.g., Abushamaa, A. M. et al. (2002) "OXIDATIVE STRESS AND INFLAMMATION CONTRIBUTE TO LUNG TOXICITY AFTER A COMMON BREAST CANCER CHEMOTHERAPY REGIMEN," Am J Physiol Lung Cell Mol Physiol. 283(2):L336-45; Chung-man, Ho J. et al. (2001) "Differential expression of manganese superoxide dismutase and catalase in lung cancer," Cancer Res. 61(23):8578-85; Senthil, K. et al. (2004) "EVIDENCE OF OXIDATIVE STRESS IN THE CIRCULATION OF OVARIAN CANCER PATIENTS," Clin Chim Acta. 339(1-2):27-32; Shacter, E. et al. (2000) "OXIDATIVE STRESS INTERFERES WITH CANCER CHEMOTHERAPY: INHIBITION OF LYMPHOMA CELL APOPTOSIS AND PHAGOCYTOSIS," Blood. 96(1):307-13; Wen, J. et al. (2002) "OXIDATIVE STRESS-MEDIATED APOPTOSIS. THE ANTICANCER EFFECT OF THE SESQUITERPENE LACTONE PARTHENOLIDE," J Biol Chem. 277(41):38954-64. Epub 2002 Jul. 31).

The present invention also relates to the use of biliverdin and its derivatives and therapeutically acceptable salts to provide cytoprotective therapy to individuals suffering from, or at risk of suffering from, Alzheimer's disease. The role of reactive oxygen in the etiology and pathology of Alzheimer's Disease has been described (see, e.g., Cummings, J. L. (2001) "TREATMENT OF ALZHEIMER'S DISEASE," Clin Cornerstone. 2001; 3(4):27-39; Grundman, M. et al. (2002) "ANTIOXIDANT STRATEGIES FOR ALZHEIMER'S DISEASE," Proc Nutr Soc. 61(2):191-202; Veurink, G. et al. (2003) "GENETICS, LIFESTYLE AND THE ROLES OF AMYLOID BETA AND OXIDATIVE STRESS IN ALZHEIMER'S DISEASE," Ann Hum Biol. 30(6):639-67).

The present invention also relates to the use of biliverdin and its derivatives and therapeutically acceptable salts to provide cytoprotective therapy to individuals suffering from, or at risk of suffering from, bacterial or viral disease. The role of reactive oxygen in the etiology and pathology of bacterial and viral disease has been described (see, e.g., Christen, S. et al. (2001) "OXIDATIVE STRESS IN BRAIN DURING EXPERIMENTAL BACTERIAL MENINGITIS: DIFFERENTIAL EFFECTS OF ALPHA-PHENYL-TERT-BUTYL NITRONE AND N-ACETYLCYSTEINE TREATMENT," Free Radic Biol Med. 31(6):754-62; Gil, L. et al. (2003) "CONTRIBUTION TO CHARACTERIZATION OF OXIDATIVE STRESS IN HIV/AIDS PATIENTS," Pharmacol Res. 47(3):217-24; Loguercio, C. et al. (2003) "OXIDATIVE STRESS IN VIRAL AND ALCOHOLIC HEPATITIS," Free Radic Biol Med. ;34(1):1-10;

Pharmaceutical Compositions of the Present Invention

One or more of the pharmaceutical compositions of the present invention (e.g., biliverdin, a biliverdin derivative or a therapeutically acceptable of either), may be used to prepare pharmaceutical compositions, either alone or with other active agents, for treating diseases and conditions associated with the presence of reactive oxygen species. The invention particularly relates to the use of biliverdin and its derivatives and therapeutically acceptable salts to prevent the onset of all such diseases and conditions in individuals or tissue at risk of such diseases and conditions as well as to the use of such molecules to attenuate the severity of all such diseases and conditions in individuals or tissue having such diseases and conditions. Thus, as used herein, the term "treatment" is intended to encompass the administration of such pharmaceutical compositions prophylactically so as to prevent the onset of a disease or condition in an individual/tissue at risk of such infection and/or therapeutically, so as to attenuate the severity of an existing disease or condition.

The pharmaceutical compositions of the present invention may be in the form of an emulsion, gel, solution, suspension, etc. In addition, the pharmaceutical composition can also contain pharmaceutically acceptable additives including, for example, diluents, binders, stabilizers, and preservatives. Administration of pharmaceutically acceptable salts described herein is preferred. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. Preferred salts include but are not limited to sodium phosphate, sodium acetate, sodium bicarbonate, sodium sulfate, sodium pyruvate, potassium phosphate, potassium acetate, potassium bicarbonate, potassium sulfate, potassium pyruvate, disodium DL-$\alpha$-glycerol-phosphate, and disodium glucose-6-phosphate. "Phosphate" salts of sodium or potassium can be either the monobasic form, e.g., NaHPO$_4$, or the dibasic form, e.g., Na$_2$HPO$_4$, but a mixture of the two, resulting in a desired pH, is most preferred.

As used herein a "salt" is a substance produced from the reaction between acids and bases which comprises a metal (cation) and a nonmetal (anion). Salt crystals may be "hydrated" i.e., contain one or more water molecules. Such hydrated salts, when dissolved in an aqueous solution at a certain molar concentration, are equivalent to the corresponding anhydrous salt dissolved in an aqueous solution at the same molar concentration. For the present invention, salts which are readily soluble in an aqueous solution are preferred.

Further, the pharmaceutical composition may be prepared in the form of admixture with one or more pharmaceutically acceptable excipients so long as such additional excipients do not interfere with the effectiveness of the peptides and the side effects and adverse reactions are not increased additively or synergistically. The pharmaceutical compositions of the present invention can be associated with chemical moieties which may improve the composition's solubility, absorption, biological half life, etc. The moieties may alternatively decrease the toxicity of the pharmaceutical compositions, eliminate or attenuate any undesirable side effect of the pharmaceutical compositions, etc. Moieties capable of mediating such effects are disclosed in Remington's Pharmaceutical Sciences, 19$^{th}$ Edition, A. R. Gennaro, ed., Mack Publishing Co., Easton, Pa. (1995). Procedures for coupling such moieties to a molecule are well known in the art.

As used herein a pharmaceutical "excipient" is a substance other than the pharmacologically active drug or prodrug which is included in the manufacturing process or are contained in a finished pharmaceutical product dosage form.

Some, for example, comprise the product's delivery system. In the preferred embodiment pharmaceutical excipients transport the active drug to the site in the body where the drug is intended to exert its action. In more preferred embodiment, excipients will keep the drug from being released too early in the assimilation process in places where it could damage tender tissue and create gastric irritation or stomach upset. In even more preferred embodiment, excipients will help the drug to disintegrate into particles small enough to reach the blood stream more quickly and still others protect the product's stability so it will be at maximum effectiveness at time of use. In order to improve patient compliance, these excipients can be used simply to make the pharmaceutical composition taste and look better (International Pharmaceutical Excipients Council of the Americas; http://www.ipecamericas.org/public/faqs).

Suitable excipients include Magnesium Stearate, Lactose, Microcrystalline Cellulose, Starch (corn), Silicon Dioxide, Titanium Dioxide, Stearic Acid, Sodium Starch Glycolate, Gelatin, Talc, Sucrose, Calcium Stearate, Povidone, Pregelatinized Starch, Hydroxy Propyl Methylcellulose, OPA products (coatings & inks), Croscarmellose, Hydroxy Propyl Cellulose, Ethylcellulose, Calcium Phosphate (dibasic), Crospovidone, Shellac (and Glaze).

Administration of the Pharmaceutical Compositions of the Present Invention

The pharmaceutical compositions of the present invention may be administered by any suitable means, for example, inhalation, or interdermally, intracavity (e.g., oral, vaginal, rectal, nasal, peritoneal, ventricular, or intestinal), intradermally, intramuscularly, intranasally, intraocularly, intraperitoneally, intrarectally, intratracheally, intravenously, orally, subcutaneously, transdermally, or transmucosally (i.e., across a mucous membrane) in a dose effective for the production of neutralizing antibody and resulting in protection from infection or disease. The pharmaceutical compositions may be in the form of single dose preparations or in multi-dose flasks. Reference is made to Remington's Pharmaceutical Sciences, 19$^{th}$ Edition, A. R. Gennaro, ed., Mack Publishing Co., Easton, Pa. (1995).

Administration can be into one or more tissues including but not limited to muscle, skin, brain, lung, liver, spleen, bone marrow, thymus, heart, e.g., myocardium, endocardium, and pericardium; lymph nodes, blood, bone, cartilage, pancreas, kidney, gall bladder, stomach, intestine, testis, ovary, uterus, rectum, nervous system, eye, gland, or connective tissue. Furthermore, in the methods of the present invention, the pharmaceutical compositions may be administered to any internal cavity of a mammal, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, and the ocular cavities. Administration may be by needle injection, catheter infusion, biolistic injectors, particle accelerators (e.g., pneumatic "needleless" injectors), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, J.Y. et al. (1999) "GENE SUTURE—A NOVEL METHOD FOR INTRAMUSCULAR GENE TRANSFER AND ITS APPLICATION IN HYPERTENSION THERAPY," Life Sciences 65:2193-2203) or topical applications during surgery. Any mode of administration can be used so long as the mode results prophylactic or therapeutic efficacy. Methods to detect such a response include serological methods, e.g., western blotting, staining tissue sections by immunohistochemical methods, and measuring the activity of the polypeptide.

In one embodiment, DNA compositions will be used to provide the preferred peptides of the present invention. Pharmaceutical DNA compositions and methods for their manufacture and delivery that may be used in accordance with the present invention are disclosed in U.S. Pat. Nos. 5,589,466; 5,620,896; 5,641,665; 5,703,055; 5,707,812; 5,846,946; 5,861,397; 5,891,718; 6,022,874; 6,147,055; 6,214,804; 6,228,844; 6,399,588; 6,413,942; 6,451,769, European Patent Documents EP 1165140A2; EP1006796A1 and EP0929536A1; and PCT Patent Publications WO00/57917; WO00/73263; WO01/09303; WO03/028632; WO94/29469; WO95/29703; and WO98/14439.

The compositions of the present invention can be lyophilized to produce pharmaceutical compositions in a dried form for ease in transportation and storage. The pharmaceutical compositions of the present invention may be stored in a sealed vial, ampoule or the like. In the case where the pharmaceutical composition is in a dried form, the composition is dissolved or suspended (e.g., in sterilized distilled water) before administration. An inert carrier such as saline or phosphate buffered saline or any such carrier in which the pharmaceutical compositions has suitable solubility, may be used.

The pharmaceutical compositions can be solubilized in a buffer prior to administration. Suitable buffers include, for example, phosphate buffered saline (PBS), normal saline, Tris buffer, and sodium phosphate vehicle (100-150 mM preferred). Insoluble polynucleotides can be solubilized in a weak acid or base, and then diluted to the desired volume with a neutral buffer such as PBS. The pH of the buffer is suitably adjusted, and moreover, a pharmaceutically acceptable additive can be used in the buffer to provide an appropriate osmolarity within the lipid vesicle. Preferred salt solutions and auxiliary agents are disclosed herein.

Compositions used in of the present invention can be formulated according to known methods. Suitable preparation methods are described, for example, in Remington's Pharmaceutical Sciences, 19$^{th}$ Edition, A. R. Gennaro, ed., Mack Publishing Co., Easton, Pa. (1995), incorporated herein by reference in its entirety. Although the composition is preferably administered as an aqueous solution, it can be formulated as an emulsion, gel, solution, suspension, lyophilized form, or any other form known in the art. According to the present invention, if the composition is formulated other than as an aqueous solution, it will require resuspension in an aqueous solution prior to administration.

Such compositions may be formulated into any of the various compositions and may be used in any of the methods disclosed herein. For aqueous compositions used in vivo, use of sterile pyrogen-free water is preferred. Such formulations will contain an effective amount of such pharmaceutical composition together with a suitable salt and/or pharmaceutically acceptable excipient as disclosed herein, in order to prepare pharmaceutically acceptable compositions suitable for optimal administration to a vertebrate.

The effective amount of a pharmaceutical composition of the present invention depends on factors including the age and weight of the subject, the delivery method and route, the type of treatment desired, and the type of pharmaceutical composition being administered. In general, an effective amount of the pharmaceutical composition of the present invention will contain from about 1 ng to about 30 mg of such pharmaceutical composition, more preferably, from about 100 ng to about 10 mg of such pharmaceutical composition. Certain preferred formulations of the present invention may include about 1 ng of such pharmaceutical composition, about 5 ng of such pharmaceutical composition, about 10 ng of such pharmaceutical composition, about 50 ng of such pharmaceutical composition, about 100 ng of such pharmaceutical composition, about 500 ng of such pharmaceutical composition, about 1 µg of such pharmaceutical compositions, about 5 µg of such pharmaceutical composition, about 10 µg of such pharmaceutical composition, about 50 µg of such pharmaceutical compositions, about 100 µg of such pharmaceutical composition, about 150 µg of such pharmaceutical composition, about 200 µg of such pharmaceutical compositions, about 250 µg of such pharmaceutical composition, about 300 µg of such pharmaceutical composition, about 350 µg of such pharmaceutical compositions, about 400 µg of such pharmaceutical composition, about 450 µg of such pharmaceutical composition, about 500 µg of such pharmaceutical composition, about 550 µg of such pharmaceutical composition, about 600 µg of such pharmaceutical composition, about 650 µg of such pharmaceutical composition, about 700 µg of such pharmaceutical composition, about 750 µg of such pharmaceutical composition, about 800 µg of such pharmaceutical composition, about 850 µg of such pharmaceutical composition, about 900 µg of such pharmaceutical composition, about 950 µg of such pharmaceutical composition, about 1 mg of such pharmaceutical composition, about 5 mg of such pharmaceutical composition, about 10 mg of such pharmaceutical composition, about 15 mg of such pharmaceutical composition, about 20 mg of such pharmaceutical composition, about 25 mg of such pharmaceutical composition, or about 30 mg of such pharmaceutical composition.

Having now generally described the invention, the same will be more readily understood through reference to the following examples, which are provided by way of illustration, and are not intended to be limiting of the present invention, unless specified.

EXAMPLE 1

Experimental Methods and Conditions

Strains, Plasmids, and Culture Conditions—Cell culture is conducted in a defined medium, yeast nitrogen base (YNB) with appropriate amino acid supplements (Sherman, F. (1991) "GETTING STARTED WITH YEAST," Methods Enzymol. 191:1-21). Iron-sufficient and -deficient media are supplied with or without 1.2 µM $FeCl_3$, respectively (Q-Biogene, Carlsbad, Calif.). Cells are cultured at 30° C. by shaking at 250 rpm with appropriate additions as indicated. Bovine methemoglobin, FAS, ferrozine, fetuin, holotransferrin, apotransferrin, and casein are obtained from Sigma Chemical Corp. Preparation and isolation of human Hb, CoPPIX-globin, and human apoglobin are obtained as described by Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118. Hemin and biliverdin standards are obtained from Frontier Scientific Porphyrin Products (Logan, Utah). Biliverdin was quantified in acidic MeOH at 377 nm using $\epsilon=66.2$ $mM^{-1}$ $cm^{-1}$ (Saito, S. et al. (1982) "VERDOHEMOCHROME IX ALPHA: PREPARATION AND OXIDOREDUCTIVE CLEAVAGE TO BILIVERDIN IX ALPHA," Proc. Natl. Acad. Sci. U.S.A. 79, 1393-1397). Hemin and Hb quantification are obtained as described by Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118. C. albicans strain YJB6284 (Bensen, E. S. et al. (2002) "A FORKHEAD TRANSCRIPTION FACTOR IS IMPORTANT FOR TRUE HYPHAL AS WELL AS YEAST MORPHOGENESIS IN CANDIDA ALBICANS," Eukaryot. Cell 1:787-798) is a prototrophic version of BWP17 and is designated herein as the "parental" strain. Both alleles of CaHMX1 are sequentially disrupted using the method of Wilson, R. et al. (1999) "RAPID HYPOTHESIS TESTING WITH CANDIDA ALBICANS THROUGH GENE DISRUPTION WITH SHORT HOMOLOGY REGIONS," J. Bacteriol. 181:1868-1874 in C. albicans strain BWP17. Arg-4 and His-1 mutagenic cassettes are constructed using the following primer sets to direct recombination to the CaHMX1 coding region:

```
                                          SEQ ID NO:2
GGCTAATAGA ATAAATCTTG AAACCAGATC TTTGCACGAT
AGAGCAGACA AGACAGTTAG TTTTCCCAGT CACGACGTT
and
                                          SEQ ID NO:3
GTGACAAACC ATCTCTTTGT GGGTACATAC CAGTAGCTTT
GAGGACCGAC GATTGTGGAA TTGTGACGCG ATA
```

C. albicans strain CAMP 49, containing disruptions of both CaHMX1 alleles, is rendered prototrophic by the insertion of plasmid pCaEXP in the RP10 locus to create CAMP 50 (Care,. R. S. et al. (1999) "THE MET3 PROMOTER: A NEW TOOL FOR CANDIDA ALBICANS MOLECULAR GENETICS," Mol. Microbiol. 34:792-798). Strain CAMP Ki-29, containing the Renilla luciferase gene under the control of the CaHMX1 promoter, is constructed using a 1.4-kb region of the CaHMX1 promoter region. This is preferably accomplished by polymerase chain reaction (PCR) using primers:

```
CTGCAGATTG TATGTGTAAT GATATATG     SEQ ID NO:4
and
CCAGCTAATA CATCGATGGC              SEQ ID NO:5
``` and cloning into pCR-BluntII TOPO (Invitrogen). The inserted fragment is then excised with SstI and PstI and cloned into plasmid pCRW3 (Srikantha, T. et al. (1996) "THE SEA PANSY RENILLA RENIFORMIS LUCIFERASE SERVES AS A SENSITIVE BIOLUMINESCENT REPORTER FOR DIFFERENTIAL GENE EXPRESSION IN CANDIDA ALBICANS," J. Bacteriol. 178:121-129) using similar sites resulting in plasmid pPt14. This plasmid was linearized at the unique KpnI site in the CaHMX1 promoter (see, FIG. 2, Panel D) to enable recombination into the CaHMX1 genomic site in the C. albicans strain Red 3/6 (Srikantha, T. et al. (1996) "THE SEA PANSY RENILLA RENIFORMIS LUCIFERASE SERVES AS A SENSITIVE BIOLUMINESCENT REPORTER FOR DIFFERENTIAL GENE EXPRESSION IN CANDIDA ALBICANS," J. Bacteriol. 178:121-129). Recombination resulted in the placement of the Renilla Lux gene immediately downstream of the genomic CaHMX1 promoter region. This knock-in procedure is desirable because the reporter plasmid pPt14 is not functional when integrated into the Ade2 locus when introduced as an episome. The resulting strain, CAMP Ki-29, is used for all reporter assays discussed herein. The correct insertion sites of the preceding constructs in the genomes of strains CAMP 50 and CAMP Ki-29 are verified by Southern blotting.

Luciferase Assays—Reporter assays use C. albicans cells that are grown at 30° C. in minimal YNB medium with ammonium sulfate and 2% glucose. $5\times10^7$ cells were harvested, cell extracts were obtained by glass bead lysis (Srikantha, T. et al. (1996) "THE SEA PANSY RENILLA RENIFORMIS LUCIFERASE SERVES AS A SENSITIVE BIOLUMINESCENT REPORTER FOR DIFFERENTIAL GENE EXPRESSION IN CANDIDA ALBICANS," J. Bacteriol. 178:121-129), and luminescence is determined using coelenterazine as a substrate (Promega). Luciferase activity is defined as the number of light units using $5\times10^7$ cells/assay point in 200 µl of lysis buffer using a 5-µl volume for light measurement. To assess regulation of the promoter by iron, the ferrous iron chelator ferrozine is added to cell cultures in the presence of FAS to buffer iron concentrations as described (Philpott, C. C. et al. (1998) "CELL-CYCLE ARREST AND INHIBITION OF G1 CYCLIN TRANSLATION BY IRON IN AFT1-1$^{UP}$ YEAST," EMBO J. 17, 5026-5036) (see also, Chaney, R. L. (1988) "PLANTS CAN UTILIZE IRON FROM IRON-N,N'-DI-2 HYDROXYBEN-ZOYLETHYLENEDIAMINE-N,N'-DIACETIC ACID, A FERRIC CHELATE WITH 1,000,000 GREATER FORMATION CONSTANT THAN IRON-ED-DHA," J. Plant Nutr. 11, 1033-1050). FAS added to 1 mM ferrozine at 10, 100, and 400 µM represents low, optimal, and high levels of iron, respectively. The effect of proteins other than Hb on the induction of the CaHMX1 promoter are tested using Ki-29 cells cultured for 15 min in iron-replete media containing each of the following at 1 mg/ml: Hb, CoPPIX-globin, holotransferrin, apotransferrin, fetuin, casein, and apoglobin.

Molecular Biology Techniques—Total yeast RNA is prepared using the hot acid phenol method (Köhrer, K. et al. (1991) "PREPARATION OF HIGH MOLECULAR WEIGHT RNA," In: YEAST GENETICS AND MOLECULAR BIOLOGY (Guthrie, C., and Fink, G. R., Eds.) 194:398-405, Academic Press, San Diego, Calif.). Yeast transformations are carried out by the lithium acetate technique (Gietz, R. D. et al. (1995) "STUDIES ON THE TRANSFORMATION OF INTACT YEAST CELLS BY THE LIAC/SS-DNA/PEG PROCEDURE," Yeast 11:355-360). Northern and Southern analyses, DNA manipulations, and sequence analysis use standard methods (Ausubel, F. M. et al. (1988) CURRENT PROTOCOLS IN MOLECULAR BIOLOGY, John Wiley & Sons, Inc., New York). Differentially expressed genes are identified by RNA arbitrarily primed PCR following the recommendations of the manufacturer (Stratagene, La Jolla, Calif.) using RNA from C. albicans strain ATCC 44807 cells grown with or without 1 mg/ml Hb. Briefly, C. albicans cells are inoculated into YNB broth with or without 62 µM (expressed as iron equivalents) hemoglobin or ferrous sulfate and grown at 26° C. for 24 h. Under these growth conditions, no germination is observed microscopic examination. For induction of the hyphal form of C. albicans, cells grown in YNB are resuspended into RPMI 1640 supplemented with 2 mM glutamine in the absence of hemoglobin and incubated 2 hours at 37° C. with shaking at 250 rpm. A 2 hour incubation converted nearly 100% of candidal cells to hyphae or pseudohyphae by microscopic examination. The "first" strand cDNA was synthesized using the arbitrary primers:

```
AATCTAGAGC TCCTCCTC      SEQ ID NO:6
AATCTAGAGC TCTCCTGG;     SEQ ID NO:7
AATCTAGAGC TCCAGCAG;     SEQ ID NO:8
                         and
CACACGCACA CGGAAGAA      SEQ ID NO:9
```

Differentially expressed products are analyzed by standard procedures (Ausubel, F. M. et al. (1988) CURRENT PROTOCOLS IN MOLECULAR BIOLOGY, John Wiley & Sons, Inc., New York).

A total of 33 ESTs that exhibit increased expression in Hb cultures, but not when supplemented with an equivalent molar concentration of iron, are cloned and sequenced. Seven are ESTs from carboxypeptidase Y, 13 are multiple hits of four genes, and the remainder are from discrete ORFs. Differential expression of the genes induced by Hb is confirmed by Northern hybridization using DNA from each EST clone as a radiolabeled probe.

Heme Oxygenase Procedures—Coupled oxidation of human Hb to generate biliverdin α and β isomers follows the methods of O'Carra, P. et al. (1969) "HAEM CATABOLISM AND COUPLED OXIDATION OF HAEMPROTEINS," FEBS Lett. 5:295-298. Briefly, 50 mg of human Hb is made to 5 mg/ml in 0.1 M sodium phosphate buffer, pH 7.0, and incubated with 20 mg of sodium ascorbate for 2 hours at 37° C. with vigorous agitation. The sample is extracted twice with equal volumes of anhydrous ethyl ether to remove unreacted heme. Biliverdin in the aqueous phase is extracted with $CHCl_3$ and concentrated by evaporation under a stream of nitrogen at room temperature. The blue-green residue is dissolved in MeOH and made to 60% with aqueous 0.1 M ammonium acetate (v/v), pH 5.2, in preparation for HPLC analysis. Coupled oxidation of heme in pyridine is used to generate all four biliverdin isomers (α, β, γ and δ) (Sano, S. et al. (1986) "ON THE MECHANISM OF THE CHEMICAL AND ENZYMIC OXYGENATIONS OF ALPHA-OXYPROTOHEMIN IX TO FE.BILIVERDIN IX ALPHA," Proc. Natl. Acad. Sci. U.S.A. 83:531-535). Hemin (15 mg) dissolved in 50% pyridine is added to 5 volumes 0.1 M sodium phosphate buffer, pH 7.0, with 10 mg of ascorbate and incubated for 16 h at 37° C. The mixture is then acidified with HCl and glacial acetic acid, and the biliverdin isomers are extracted twice into $CHCl_3$ and concentrated by evaporation under nitrogen. The compounds are further purified on a C-18 Sep-Pak column (Millipore, Bedford, Mass.) as described below.

Biliverdin is extracted from cell pellets by suspension in an equal volume of MeOH, vortexing for 30 s, and centrifuging for 10 min at 5000×g at room temperature. The supernatant of this extraction is made to 60% with aqueous 0.1 M ammonium acetate, pH 5.2, and loaded onto a C-18 Sep-Pak column that has been sequentially preconditioned with 5 ml of MeOH, 5 ml of $H_2O$, and 15 ml of Buffer A (60% 0.1 M ammonium acetate, pH 5.2, 40% MeOH v/v). The column is then washed with 5 ml of 0.1 M ammonium acetate, pH 5.2, 5 ml of Buffer A, and the green-blue material is eluted with 2 ml of 100% MeOH. An equal volume of $CHCl_3$ is added, and the mixture is then evaporated under nitrogen. Cell supernatants are extracted by adding 0.6 volumes of concentrated ammonium acetate, pH 5.2, and then making the mixture 40% in MeOH. Biliverdin is isolated on a C-18 Sep-Pak as described above. Biliverdin and hemin are quantified using a C-18 Alltech absorbosphere column (Deerfield, Ill.) (150×4.6 mm, 5 µm of octadecyl-silica packing) controlled by a Peak Net chromatography work station (Dionex, Sunnyvale, Calif.). The mobile phase consists of Buffer A with a gradient to 100% MeOH from 2 to 18 min at a flow rate of 1 ml/min. Absorbance is measured at 385 nm, and peaks are analyzed using Peak Net software.

EXAMPLE 2

Identification of CaHMX1 and Its Regulation by Hemoglobin

Figure 2:
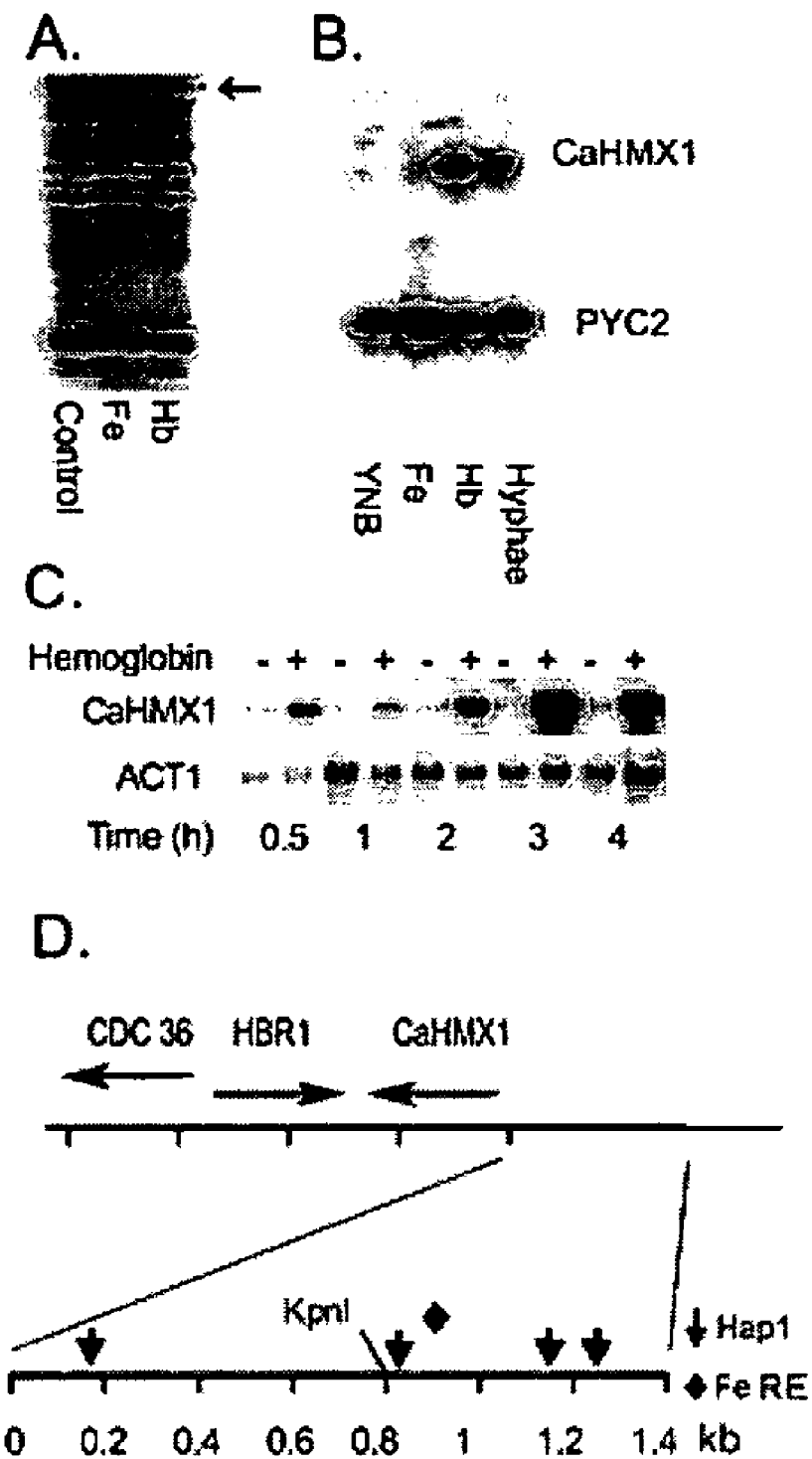
FIG. 2 show that heme oxygenase is transcriptionally activated by hemoglobin. Panel A shows differential display PCR identification of iron- and hemoglobin-induced genes. Hemoglobin-induced gene transcripts (Hb) are identified by comparison with cDNA from a non-induced control culture, and ferrous sulfate-induced cultures (Fe) were amplified using the primer (SEQ ID NO:1) CACACGCACA CGGAAGAA. In the Figure, the arrow indicates the band excised to isolate the expressed sequence tag ("EST") SY29 (CaHMX1). Panel B shows the results of northern analysis using 25 µg of total RNA from cells grown in yeast nitrogen base ("YNB"), YNB+ferrous sulfate (Fe), YNB+1 mg/ml hemoglobin (Hb), or induced to form hyphae. The blot was hybridized with DNA probes for the CaHAMX1 EST or pyruvate carboxylase 2 (PYC2). Panel C shows the results of steady state mRNA analysis of CaHMX1 is increased in the presence of hemoglobin. Northern analysis of total RNA (15 µg) harvested from *C. albicans* cells cultured with (+) or without (−) 1 mg/ml bovine methemoglobin in iron-sufficient SD medium (Sherman, F. (1991) *Methods Enzymol.* 191, 1-21), 2% glucose at 30° C. The blot was probed using a radio-labeled CaHMX1 coding region probe and reprobed with a CaACT1 probe after stripping. Panel D provides a diagram of the CaHMX1 gene region. Gene names or contig (i.e., group of overlapping clones) number (orf6) from the Stanford data base (http://sequence.stanford.edu/group/*candida*/) or gene numbers (IPF) from the Pasteur Institute *Candida* data base (http://genolist.pasteur.fr/CandidaDB) are listed to identify hypothetical open reading frames ("ORFs") CDC36, HBR1 (IPF8372, orf6.7618), and CaHMX1 (IPF8374, orf6.8374). Arrows indicate the direction of transcription. The lower part of Panel D provides a diagram of the CaHMX1 promoter region used to construct the luciferase reporter strain CAMP Ki-29. Indicated regulatory regions are hypothetical. Fe RE, iron-responsive element.

Genes specifically induced by Hb but not by equivalent molar concentrations of inorganic iron are identified using random arbitrarily primed PCR (FIG. 2, Panel A). RNA isolated from cells cultured for 24 h at 24° C. in the presence or absence of Hb identifies a total of 33 ESTs that exhibited increased expression in Hb cultures but not when supplemented with iron. One such EST (FIG. 2, Panel A, arrow), which was verified by Northern hybridization to be induced by Hb and not by iron or hyphal differentiation (FIG. 2, Panel B), overlappes the 3'-end of the CaHMX1 gene in the *C. albicans* genomic data base (FIG. 2, Panel D).

CaHMX1 has been identified as an iron- and hemin-regulated gene that is essential for survival with hemin as the sole iron source (Santos, R. et al. (2003) "HAEMIN UPTAKE AND USE AS AN IRON SOURCE BY *CANDIDA ALBICANS*: ROLE OF CAHMX1-ENCODED HAEM OXYGENASE," Microbiology 149:579-588). CaHMX1 is therefore characterized by measuring its steady state mRNA in the presence and absence of Hb under iron sufficiency to verify the results obtained through RNA arbitrarily primed PCR screening. *C. albicans* SC5314 cells (Fonzi, W. A. et al. (1993) "ISOGENIC STRAIN CONSTRUCTION AND GENE MAPPING IN *CANDIDA ALBICANS*," Genetics 134: 717-728) in early stationary phase growth are transferred to Hb-containing medium, and samples are harvested for RNA isolation at the indicated times (FIG. 2, Panel C). *C. albicans*, designation SC5314, was deposited on Dec. 20, 2002 with the American Type Culture Collection (ATCC) depository, 10801 University Blvd., Manassas, Va. 20110, and has ATCC Number MYA-2876. An increased mRNA level is evident as early as 30 min after Hb addition, and the level increased 10-15-fold at 3 h (FIG. 2, Panel C). These data indicate that accumulation of CaHMX1 mRNA is increased by hemoglobin under iron sufficiency.

EXAMPLE 3

CaHMX1 Transcription is Regulated by Hemoglobin as well as Iron Deficiency

Accumulation of CaHMX1 mRNA within 30 min following Hb addition suggests transcriptional regulation (FIG. 2, Panel C). To measure active transcription during the early stages of Hb exposure, a luciferase reporter gene driven by the CaHMX1 promoter is constructed. A 1.4-kb region upstream of the CaHMX1-predicted translational start site (FIG. 2, Panel D) was cloned in the *Renilla* luciferase reporter plasmid pCRW3 (Srikantha, T. et al. (1996) "THE SEA PANSY *RENILLA RENIFORMIS* LUCIFERASE SERVES AS A SENSITIVE BIOLUMINESCENT REPORTER FOR DIFFERENTIAL GENE EXPRESSION IN *CANDIDA ALBICANS*," J. Bacteriol. 178:121-129). This region contains four HAP1 consensus sites (Zhang, L. et al. (1994) "THE YEAST ACTIVATOR HAP1—A GAL4 FAMILY MEMBER—BINDS DNA IN A DIRECTLY REPEATED ORIENTATION," Genes Dev. 8:2110-2119) as well as a single predicted iron-responsive element (Yamaguchi-Iwai, Y. et al. (1996) "Iron-Regulated DNA Binding By The AFT1 Protein Controls The Iron Regulon In Yeast," EMBO J. 15, 3377-3384) (FIG. 2, Panel D, Fe RE). The plasmid is initially introduced into the *C. albicans* strain Red 3/6 (Srikantha, T. et al. (1996) "THE SEA PANSY *RENILLA RENIFORMIS* LUCIFERASE SERVES AS A SENSITIVE BIOLUMINESCENT REPORTER FOR DIFFERENTIAL GENE EXPRESSION IN *CANDIDA ALBICANS*," J. Bacteriol. 178:121-129) by recombination into the neutral Ade2 locus. However, expression from this construct cannot be detected. For this reason, the reporter plasmid is recombined into the genomic CaHMX1 to generate the knock-in strain CAMP Ki-29 (see Example 1). In this strain, the entire genomic region upstream of the CaHMX1 ATG can serve to supply promoter elements for the introduced *Renilla* luciferase (FIG. 2, Panel D). Similar knock-ins have been used successfully in *C. albicans* (Srikantha, T. et al. (1995) "THE FREQUENCY OF INTEGRATIVE TRANSFORMATION AT PHASE-SPECIFIC GENES OF *CANDIDA ALBICANS* CORRELATES WITH THEIR TRANSCRIPTIONAL STATE," Mol. Gen. Genet. 246:342-352).

Strain CAMP Ki-29 is first tested for responsiveness to Hb in iron-sufficient medium. Within 2.5 min following the addition of Hb, luciferase activity increased more than 10-fold over the non-induced control, and this level was sustained almost to the end of the test period (FIG. 3, Panel A). These data indicate that Hb binding to its cell surface receptor (Pendrak, M. L. et al. (2000) "STRUCTURAL REQUIREMENTS FOR HEMOGLOBIN TO INDUCE FIBRONECTIN RECEPTOR EXPRESSION IN *CANDIDA ALBICANS*," Biochemistry 39:16110-16118) induces a signal that rapidly increases transcription to the CaHMX1 promoter under iron-replete conditions.

To ensure that this induction is specific for Hb, several control proteins are tested for their ability to stimulate luciferase activity in strain Ki-29 (Table 1). The cobalt analog of Hb, CoPPIX-globin, has equivalent activity to Hb, but apoglobin is inactive. Therefore, the iron in Hb is not essential for activity, but the native conformation of globin induced by porphyrin binding is required. These results are consistent with the previous report that CoPPIX-globin stimulated expression of a fibronectin receptor in *C. albicans* to the same extent as Hb, whereas globin was inactive (Pendrak, M. L. et al. (2000) "STRUCTURAL REQUIREMENTS FOR HEMOGLOBIN TO INDUCE FIBRONECTIN RECEPTOR EXPRESSION IN *CANDIDA ALBICANS*," Biochemistry 39:16110-16118). None of the other proteins tested significantly induce luciferase activity above the control, but the ferroprotein transferrin somewhat decreased the basal activity of the CaHMX1 promoter (Table 1). These proteins also failed to induce the expression of the fibronectin receptor in *C. albicans* (Yan, S., et al. (1996) "SPECIFIC INDUCTION OF FIBRONECTIN BINDING ACTIVITY BY HEMOGLOBIN IN *CANDIDA ALBICANS* GROWN IN DEFINED MEDIA," Infect. Immun. 64, 2930-2935). The data presented in Table 1 is obtained by culturing *C. albicans* strain Ki-29 in iron-replete medium at 30° C. for 15 min in the presence of 1 mg/ml of the indicated proteins; luciferase activities expressed as mean±S.D. are from two separate experiments.

TABLE 1

| Protein | Luciferase Activity |
| --- | --- |
| None | 41.7 ± 13.5 |
| Hb | 144.7 ± 11 |
| CoPPIX-globin | 161.7 ± 24 |
| Apo-globin | 57.6 ± 2.1 |
| Holo-transferrin | 20.7 ± 0.55 |
| Apo-transferrin | 64.4 ± 11.8 |
| Fetuin | 59.3 ± 5.9 |
| Casein | 38.6 ± 8.1 |

Although the iron in Hb is not required to induce CaHMX1 transcription, steady state CaHMX1 mRNA has been reported to be increased by iron deficiency and by hemin at 5 hour post-transfer to new medium (Santos, R. et al. (2003) "HAEMIN UPTAKE AND USE AS AN IRON SOURCE BY *CANDIDA ALBICANS*: ROLE OF CAHMX1-ENCODED HAEM OXYGENASE," Microbiology 149:579-588). For this reason, promoter activity is tested over an extended time course using Hb under iron-sufficient and -deficient conditions. Hb rapidly increased promoter activity independent of the iron status of the medium (FIG. 3, Panel B, circles). Neither iron deficiency nor hemin addition increased promoter activity at the early time points, but both showed induction after a lag time of 3 h (FIG. 3, Panel B). Taken together, Table 1 and FIG. 3 indicate that the effects of Hb, iron deficiency, and hemin on CaHMX1 transcription are separable events.

Figure 4:
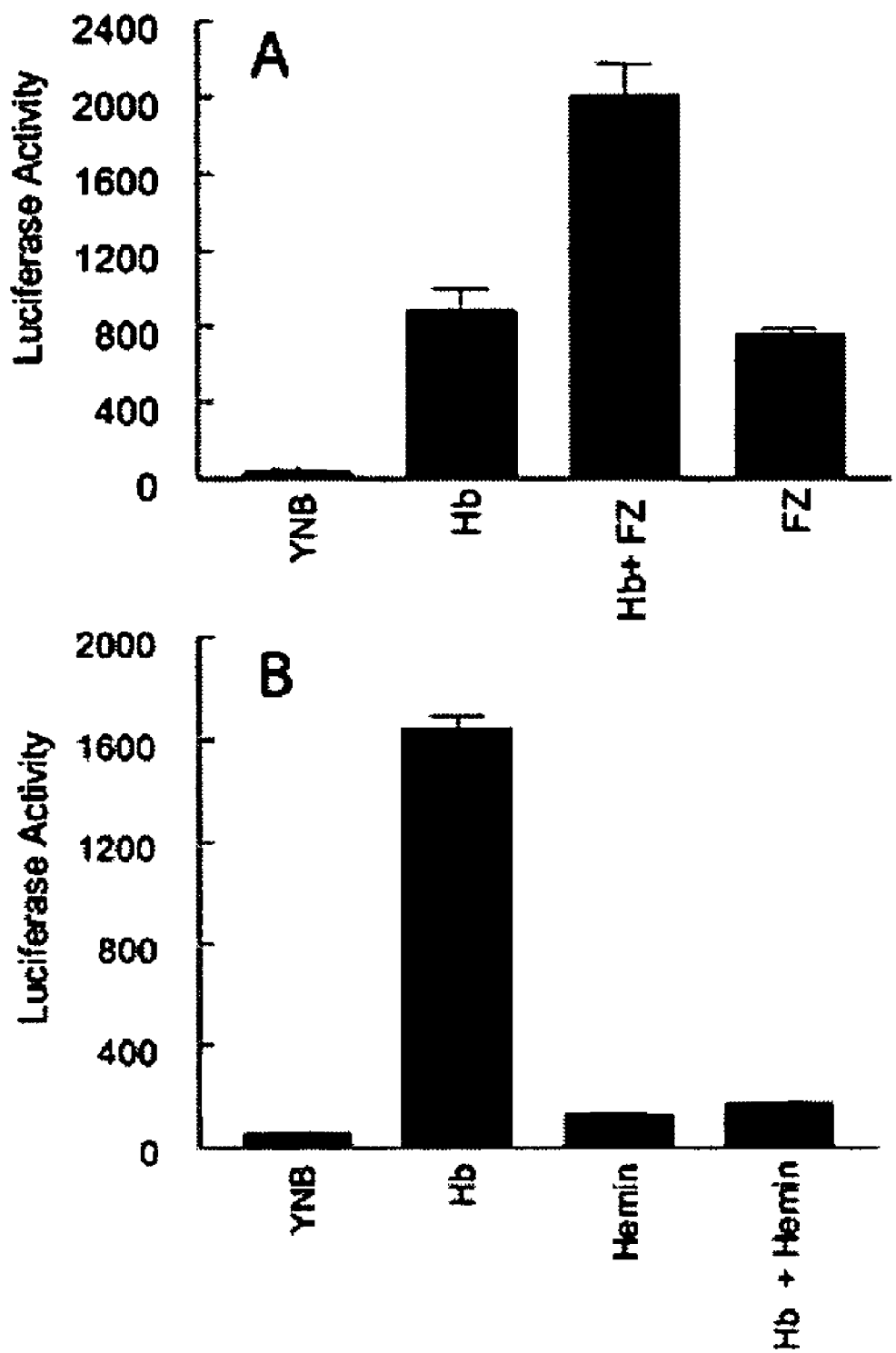
FIG. 4 shows that iron and hemin differentially affect Hb activation of CaHMX1 transcription. Panel A, strain Ki-29 cells are cultured for 24 h in iron-deficient medium containing 10 μM ferrous ammonium sulfate ("FAS"). Equivalent cell numbers are harvested for luciferase measurement: Hb, 25 μM; FZ, 100 μM ferrozine; Hb+Fz, 100 μM ferrozine and 25 μM Hb. Panel B, hemin dampens Hb activation of CaHMX1 transcription. Ki-29 cells are cultured in iron-deficient medium containing 10 μM FAS with 100 μM ferrozine for 24 h before sampling for luciferase activity. Hemin and Hb are added at 25 μM. Results are presented ±S.D. and n=3.

CaHMX1 was initially identified as a Hb-regulated gene by RNA arbitrarily primed PCR analysis using RNA isolated 24 h after the addition of Hb (see Example 1). To examine the iron dependence of the Hb response for CaHMX1 at later times, these conditions are duplicated with the CAMP Ki-29 reporter strain (FIG. 4). After cell culture for 24 h, iron-replete conditions maintained the promoter in an inactive state, but the addition of Hb stimulated activity ~40-fold at this time (FIG. 4, Panel A). When ferrozine is added to generate iron deficiency, a similar induction of promoter activity is seen (FIG. 4, Panel A). However, ferrozine and Hb together produce an additive effect and result in transcriptional activity greater than either compound added alone (FIG. 4, Panel A). This synergistic activity further indicates that Hb and iron depletion are distinct signals that regulate the CaHMX1 promoter.

The presence of four HAP1 consensus sites (Zhang, L. et al. (1994) "THE YEAST ACTIVATOR HAP1—A GAL4 FAMILY MEMBER—BINDS DNA IN A DIRECTLY REPEATED ORIENTATION," Genes Dev. 8:2110-2119) 5' of CaHMX1 (FIG. 2, Panel D) suggested that hemin could play a direct role in the regulation of this promoter. However, hemin addition to CAMP Ki-29 cells increases activity only about 2-fold after 24 h, in contrast to the high activity of the combination of Hb and ferrozine (FIG. 4, Panel B). Surprisingly, however, the inducing activity of Hb combined with ferrozine is suppressed by the addition of hemin and results in only a 2.5-fold increase in activity over the iron-replete control (FIG. 4, Panel B). Therefore, hemin is unlikely to be the mediator of CaHMX1 induction by Hb and may be a negative regulator of CaHMX1 under some conditions.

EXAMPLE 4

CaHMX1 is Necessary for Growth Under Iron Deficiency

Figure 5:
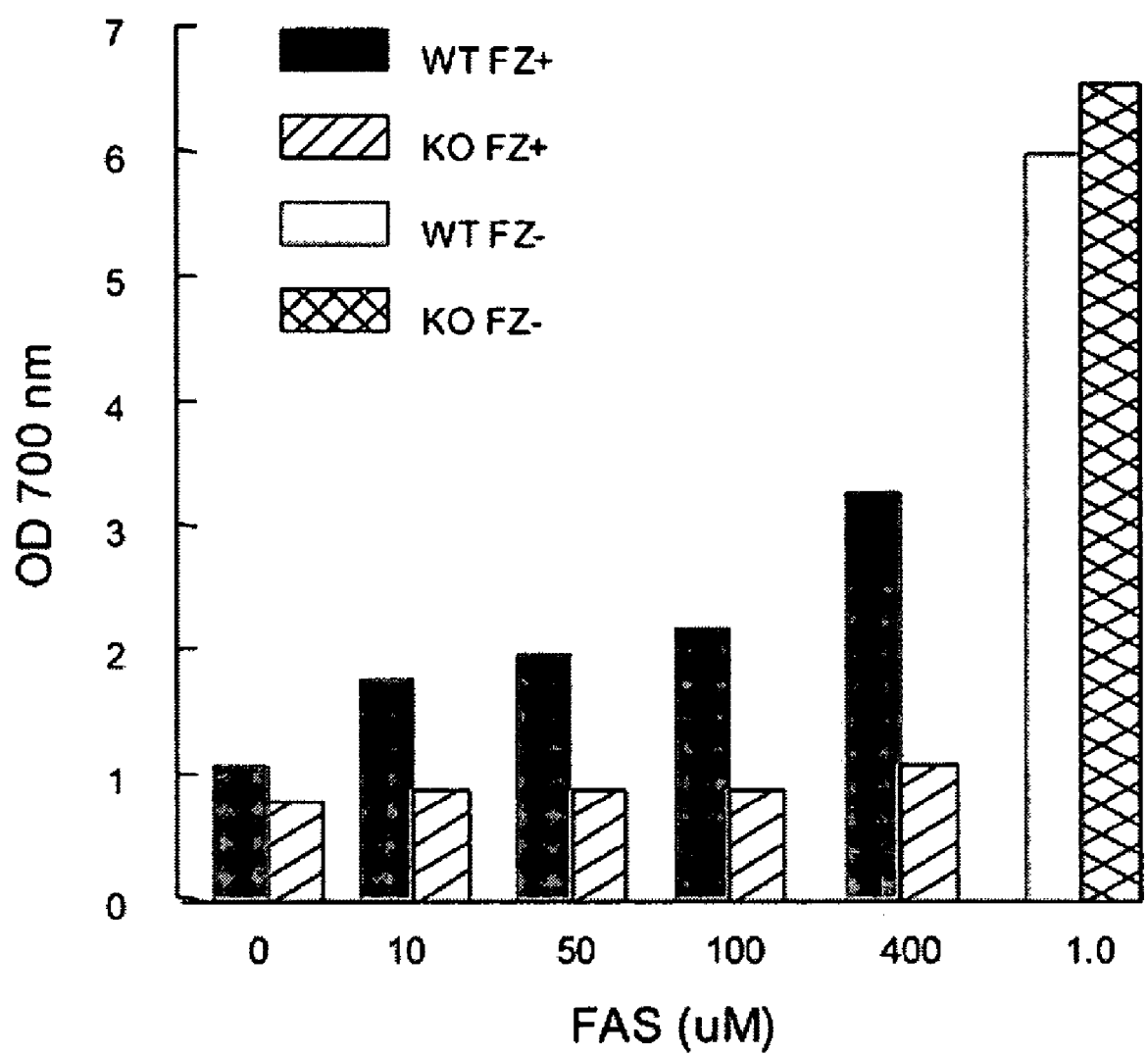
FIG. 5 demonstrates that a CaHMX1 null mutation affects cell growth under iron deficiency. YJB6284 (parental) or CAMP 50 (CaHMX1 −/−) cells are cultured in the presence (FZ+) or absence (FZ−) of 100 μM ferrozine. FAS is added at the indicated concentrations. A duplicate experiment gave similar results.

Acquisition of iron is clearly essential for cell survival (Weinberg, E. D. (1999) "THE ROLE OF IRON IN PROTOZOAN AND FUNGAL INFECTIOUS DISEASES," J. Eukaryot. Microbiol. 46:231-238). The interplay of iron and Hb regulation at the CaHMX1 promoter suggests a role for this gene in cellular iron metabolism. The *S. cerevisiae* ortholog HMX1 plays a role in the mobilization of iron from internal heme stores, indicating a direct connection of HMX1 to iron metabolism (Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278:36582-36587). To test whether cell growth depended upon CaHMX1 activity, survival of parental and homozygous deletion strains are compared under various levels of iron sufficiency. The deletion mutant grows at an equivalent rate and produces a stationary cell density equivalent to those of the parental strain in iron-replete medium (FIG. 5). Growth of both strains is suppressed in the presence of ferrozine to generate iron deficiency. However, titration of iron into the medium by the addition of FAS (Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278:36582-36587) permits growth of the parental strain but not of the CaHMX1 deletion mutant under iron restriction (FIG. 5). Addition of 100 µM FAS approximates optimal physiological iron conditions (Philpott, C. C. et al. (2002) "THE RESPONSE TO IRON DEPRIVATION IN *SACCHAROMYCES CEREVISIAE*: EXPRESSION OF SIDEROPHORE-BASED SYSTEMS OF IRON UPTAKE," Biochem. Soc. Trans. 30:698-702). Therefore, a step in iron assimilation that becomes rate-limiting only at low iron concentrations requires CaHmx1p.

EXAMPLE 5

CaHMX1 Displays a Heme Oxygenase Signature in Its Primary Sequence

The CaHmx1p coding region has 36% identity and 49% similarity to the hypothetical heme oxygenase in *S. cerevisiae* (Hmx1) (Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278:36582-36587). A comparison of the CaHMX1 coding region (SEQ ID NO: 10):

```
MQYKSSGATS KLSQVEIIPA KTDVGALANR INLETRSLHD RADKTVTLKF

ALALRNYKVY RQGLQAFYHV FASIEKALYR QLEKKDEWSE MLEQVWKPEI

ARAGKAEQDL LFFYDDNKEK FIKPIMPAQI EFCKHILEVT EEKPYLLFAY

LHVMYLALFA GGRIMRSSVL KATGMYPQRD GLSHDDVVRM GTNFFTFDVP

DEDLLRLTYK RDYELVTRNG LTEEQKLEII EESKYIFEHD TKCVAELEKH

NMDKLSGTWT YFLVTRGYYA ALVLFSLLAL IYLRRVVNKL T
``` with the human isoform-1 (SEQ ID NO:11):

```
MERPQPDSMP QDLSEALKEA TKEVHTQAEN AEFMRNFQKG QVTRDGFKLV

MASLYHIYVA LEEEIERNKE SPVFAPVYFP EELHRKAALE QDLAFWYGPR

WQEVIPYTPA MQRYVKRLHE VGRTEPELLV AHAYTRYLGD LSGGQVLKKI

AQKALDLPSS GEGLAFFTFP NIASATKFKQ LYRSRMNSLE MTPAVRQRVI
```

-continued

```
EEAKTAFLLN IQLFEELQEL LTHDTKDQSP SRAPGLRQRA SNKVQDSAPV

ETPRGKPPLN
``` for which the crystal structure has been determined, show 25% identity and 38% similarity. The landmarks comprising a heme oxygenase signature in the primary sequence are highly conserved (FIG. 6). In the heme-binding pocket in heme oxygenases, heme is positioned between the proximal and distal helices (Schuller, D. J. et al. (1999) "CRYSTAL STRUCTURE OF HUMAN HEME OXYGENASE-1," Nat. Struct. Biol. 6:860-867). The proximal region of the heme-binding pocket, which contains residues that make direct heme contact, is present in the Candida hypothetical protein (FIG. 6, filled ovals). His-25, Ala-28, Glu-29, and Phe-33 in helix 1 as well as Phe-207 located in helix 7 of the human heme oxygenase structure (Schuller, D. J. et al. (1999) "CRYSTAL STRUCTURE OF HUMAN HEME OXYGENASE-1," Nat. Struct. Biol. 6:860-867) are all positioned appropriately when aligned with the Candida sequence. The conservative E29D change is the only deviation (FIG. 6, filled ovals). In the closely related S. cerevisiae protein, His-25 is altered to Ala (Protchenko, O. et al. (2003) "REGULATION OF INTRACELLULAR HEME LEVELS BY HMX1, A HOMOLOGUE OF HEME OXYGENASE, IN SACCHAROMYCES CEREVISIAE," J. Biol. Chem. 278:36582-36587). This particular mutation in the human HO-1 protein renders the enzyme non-functional (Sun, J. et al. (1994) "IDENTIFICATION OF HISTIDINE 25 AS THE HEME LIGAND IN HUMAN LIVER HEME OXYGENASE," Biochemistry 33:13734-13740) and may account for an inability to demonstrate biliverdin synthesis catalyzed by the S. cerevisiae protein (Auclair, K. et al. (2003) "CLONING AND EXPRESSION OF A HEME BINDING PROTEIN FROM THE GENOME OF SACCHAROMYCES CEREVISIAE," Protein Expression Purif. 28:340-349). An additional region not directly associated with the proximal helix, but unique to heme oxygenases, allows Gly-139 and Gly-144 to directly contact the heme (Schuller, D. J. et al. (1999) "CRYSTAL STRUCTURE OF HUMAN HEME OXYGENASE-1," Nat. Struct. Biol. 6:860-867). The corresponding residues in CaHmx1p are Ala and Gly, respectively (FIG. 6, filled triangles). The G139A change in the Candida sequence, although absent in the majority of heme oxygenases, also occurs in the functional Arabidopsis enzyme (Muramoto, T. et al. (2002) "EXPRESSION AND BIOCHEMICAL PROPERTIES OF A FERREDOXIN-DEPENDENT HEME OXYGENASE REQUIRED FOR PHYTOCHROME CHROMOPHORE SYNTHESIS," Plant Physiol. 130, 1958-1966). Thus, this probably represents a neutral change (Schuller, D. J. et al. (1999) "CRYSTAL STRUCTURE OF HUMAN HEME OXYGENASE-1," Nat. Struct. Biol. 6:860-867).

In the crystal structure of human heme oxygenase protein, the α meso-edge of heme is positioned near a hydrophobic wall comprising Met-34, Phe-37, and Phe-214 (Schuller, D. J. et al. (1999) "CRYSTAL STRUCTURE OF HUMAN HEME OXYGENASE-1," Nat. Struct. Biol. 6:860-867). All are represented in the Candida sequence as substitutions to smaller hydrophobic residues (FIG. 6, filled circles), although Met-34 in human isoform-2 possesses a Val substitution (Schuller, D. J. et al. (1999) "CRYSTAL STRUCTURE OF HUMAN HEME OXYGENASE-1," Nat. Struct. Biol. 6:860-867). Similar substitutions are found to occur in the functional HmuO protein from C. diphtheriae except for Phe-214, which is retained (Schmitt, M. P. (1997) "UTILIZATION OF HOST IRON SOURCES BY CORYNEBACTERIUM DIPHTHERIAE: IDENTIFICATION OF A GENE WHOSE PRODUCT IS HOMOLOGOUS TO EUKARYOTIC HEME OXYGENASES AND IS REQUIRED FOR ACQUISITION OF IRON FROM HEME AND HEMOGLOBIN," J. Bacteriol. 179:838-845). The γ meso-edge of the heme and the heme propionate residues interact with residues of the distal helix. Most all of the participating basic amino acids are represented in the Candida sequence as conservative changes of K22R, K179R, and R183K (FIG. 6, arrows), although a non-conservative substitution occurs at K18N (Gln in S. cerevisiae). Y137 is fully conserved (FIG. 6, arrow).

A highly polar region of the human heme oxygenase pocket involved in ligand discrimination (Schuller, D. J. et al. (1999) "CRYSTAL STRUCTURE OF HUMAN HEME OXYGENASE-1," Nat. Struct. Biol. 6:860-867) have the following substitutions: N210D (identical in HmuO and Hmx1p), R136M (Leu in Hmx1p), D140L (Leu in Hmx1p), and the conservative substitutions Y58F and Y114F (FIG. 6, inverted open triangles). In all of the regions that define the heme oxygenase signature at the level of the primary sequence, 58% of the C. albicans residues are identical to the human isoform-1, and this increases to 79% when conservative substitutions are included. The 21% of the residues not conserved are primarily located in the polar region of the pocket (FIG. 6).

EXAMPLE 6

Figure 9:
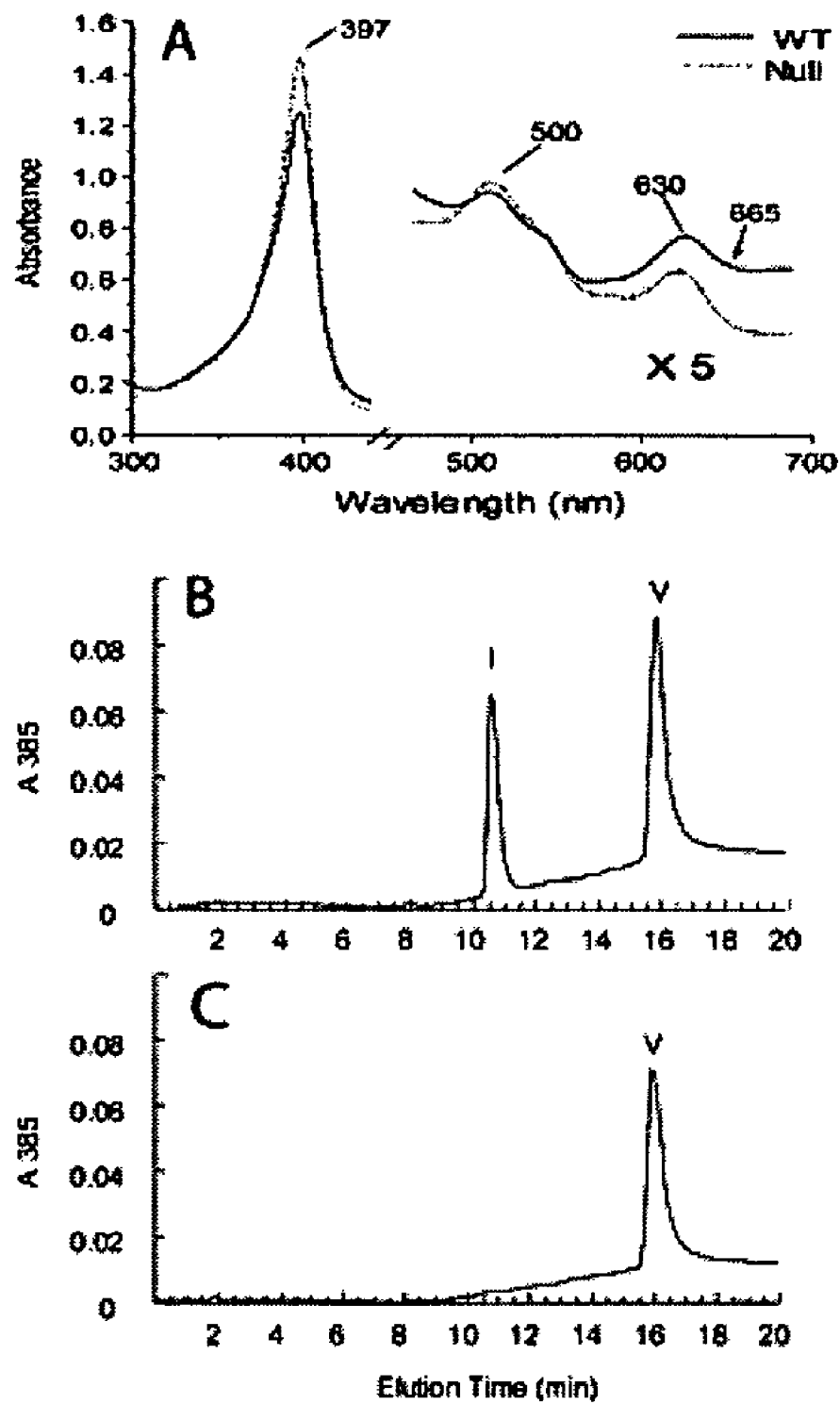
FIG. 9 demonstrates that CaHmx1p is necessary for production of the biliverdin αisomer during cell culture with Hb and hemin. YJB6284 (parental) or CAMP 50 (CaHMX1 −/−) cells are cultured for 48 hours at 30° C. with aeration in the presence of hemin (25 μM) and Hb (25 μM) under iron-deficient conditions. Cell pellets are extracted after centrifugation with acidified methanol (MeOH) and directly scanned at 600 nm/min. Panel A, wavelength scan of MeOH extracts from strains YJB6284 (solid trace) and CAMP 50 (dotted trace). Numbers above curves indicate the wavelength of absorbance maxima except for the indicated plateau starting at 665 nm. Cell extracts are further purified using a C-18 solid support and chromatographed by high pressure liquid chromatography ("HPLC") using a C-18 Alltech absorbosphere column. The mobile phase consisted of 40% MeOH in 0.1 M ammonium acetate, pH 5.2, and a linear gradient from 2 to 18 min to 100% MeOH. Panel B, YJB6284, MeOH cell pellet extract. Panel C, CAMP 50, MeOH cell pellet extract.

CaHmx1p Possesses Heme Oxygenase Activity and Generates α-Biliverdin Exclusively To determine whether CaHmx1p possesses heme oxygenase activity, genomic deletions are generated of both CaHMX1 alleles in C. albicans strain BWP17 (Wilson, R. B. et al. (1999) "RAPID HYPOTHESIS TESTING WITH CANDIDA ALBICANS THROUGH GENE DISRUPTION WITH SHORT HOMOLOGY REGIONS," J. Bacteriol. 181, 1868-1874) to produce a negative control strain. The culture of parental (YJB6284) and null CAMP 50 (CaHMX1 −/−) cells overnight in the presence of Hb and hemin results in media with distinct colors. Although the null strain retained the brown-green color of the added heme and Hb, YJB6284 cells generated a distinctly blue-green medium. After centrifugation of the culture, the majority of the blue compound remains associated with the cell pellet. Extraction of the cell pellets with MeOH and determination of their visible spectra in acidic MeOH demonstrate an increase in adsorbance beyond 550 nm that is maximal at 650-700 nm, which is typical of biliverdin in this solvent (McDonagh, A. F. et al. (1980) "PREPARATION AND PROPERTIES OF CRYSTALLINE BILIVERDIN IX ALPHA. SIMPLE METHODS FOR PREPARING ISOMERICALLY HOMOGENEOUS BILIVERDIN AND [$^{14}$C [BILIVERDIN BY USING 2,3-DICHLORO-5,6-DICYANOBENZOQUINONE," Biochem. J. 189:193-208) (FIG. 9, Panel A).

The blue-green pigment was subjected to HPLC analysis to confirm its identity as biliverdin. The HPLC elution profile reveals two peaks for the parental strain extract (FIG. 9, Panel B) but only a single peak for the CaHMX1 deletion strain (FIG. 9, Panel C). Therefore, CaHAM1 is necessary for the generation of the product in peak I. Under the same growth conditions, no reaction is observed using S. cerevisiae strains S150-2B (Mayer, S. A. et al. (1991) "YEAST CBP1 MRNA 3'END FORMATION IS REGULATED DURING THE INDUCTION OF MITOCHONDRIAL FUNCTION," Mol. Cell. Biol. 11, 813-821) and YPH 499 (Protchenko, O. et al. (2003) "REGULATION OF INTRACELLULAR HEME LEVELS BY HMX1, A HOMOLOGUE OF HEME OXYGENASE, IN SACCHAROMYCES CEREVISIAE," J. Biol. Chem. 278: 36582-36587), indicating the species specificity of the reaction.

Figure 10:
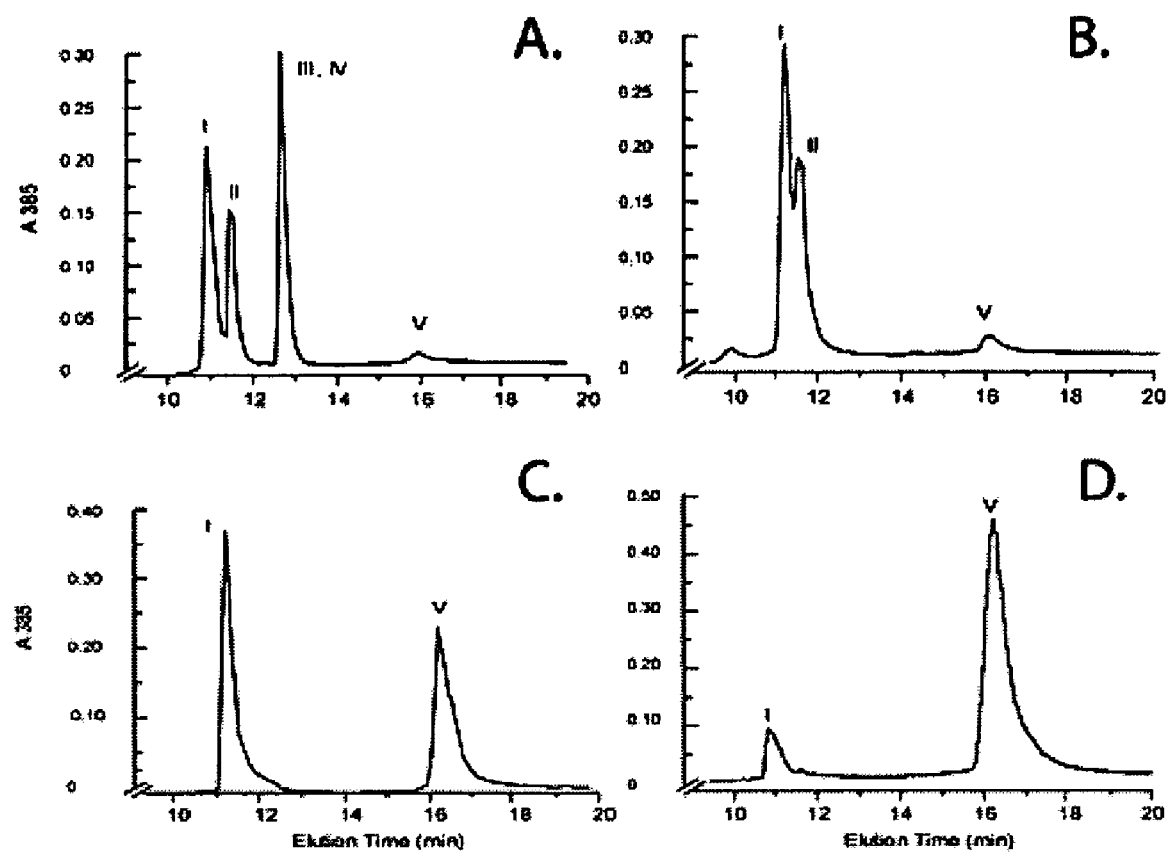
FIG. 10 demonstrates that CaHmx1p catalyzes the formation of α-biliverdin from Hb. Biliverdin isomers for standards were generated by coupled oxidation reactions with ascorbate (see Example 1). Panel A, hemin-coupled oxidation products. Panel B, Hb-coupled oxidation products. Panel C, standards, biliverdin (25 nmol) and hemin (12.5 nmol). Peak identification: I, α-biliverdin; II, β-biliverdin; III and IV, a mixture of δ- and γ-biliverdin isomers; V, hemin; γ and δ isomers cannot be resolved in this solvent system. Panel D, MeOH extract from strain YJB6284 grown in the presence of Hb (25 μM) in iron-sufficient media for 48 hours.

Comparison of the elution times of these peaks with commercial biliverdin and hemin standards confirmed that peaks I and V represented biliverdin and hemin, respectively (FIG. 10, Panel C). To identify the isomer of biliverdin in peak I, we performed coupled oxidation reactions of heme in pyridine to produce all four isomers (FIG. 10, Panel A) and of Hb to generate a mixture of α and β isomers (O'Carra, P. et al. (1969) "HAEM CATABOLISM AND COUPLED OXIDATION OF HAEMPROTEINS," FEBS Lett. 5:295-298) (FIG. 10, Panel B, peaks I and II, respectively). The product isolated from the cells coincided with the biliverdin α meso-isomer peak (compare FIG. 9, Panel B with FIG. 10, Panels A and B). The addition of Hb alone to YJB6284 cell cultures in iron-replete medium also generated the α-biliverdin isomer (FIG. 10, Panel D). Thus, strain YJB6285 cells can utilize either exogenous heme or Hb to exclusively produce the αisomer of meso-biliverdin. This confirms that C. albicans possesses a true heme oxygenase activity and that the CaHMX1 gene encodes this enzyme.

Figure 7:
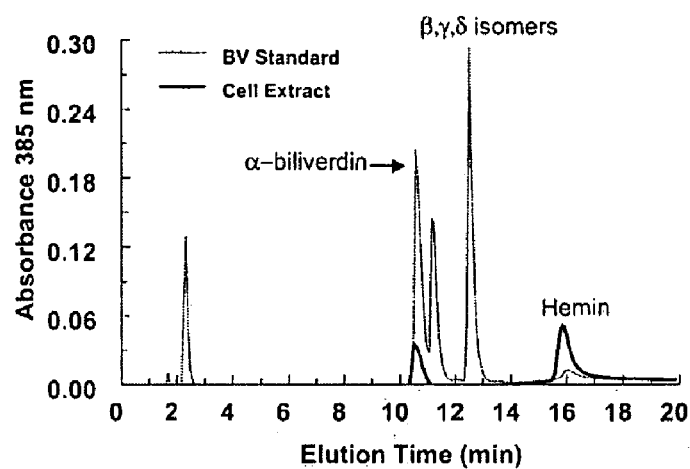
FIG. 7 shows that the methods of biliverdin production of the present invention results in the isolation of the α-biliverdin isomer.

As an additional demonstration that only the α-biliverdin isomer is produced, C. albicans wild-type strain Y JB6284 yeast cells are cultured in defined, minimal medium containing glucose and 100 μM hemin. After centrifugation, cell pellets are extracted with methanol and biliverdin is purified using solid phase extraction (C-18 Sep-Pak cartridges). Biliverdin and hemin are quantified using HPLC on an ODS column in 60% 0.1 M ammonium acetate, pH 5:40% methanol followed by a gradient to 100% methanol. A biliverdin standard obtained from Porphyrin Products, Logan, Utah identified five prominent peaks. In this chromtographic system, the biliverdin isomers elute in the order α, β, γ, δ. The product purified from the cell extract identifies the α-biliverdin isomer (10.4 min) and residual hemin (16 min) (FIG. 7).

Figure 8:
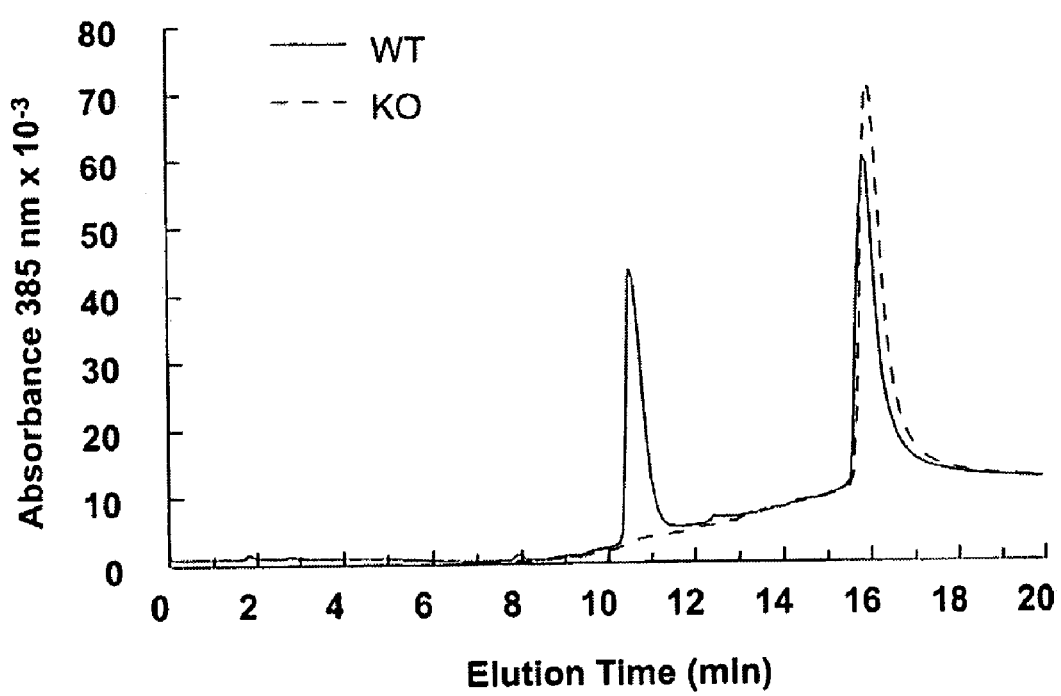
FIG. 8 shows that by deleting the gene responsible for biliverdin production from hemin, heme oxygenase(HBO-1) that the strain no longer converts hemin to biliverdin.

As a further demonstration that the C. albicans heme oxygenase gene (HBO-1) directs biliverdin production, C. albicans wild-type strain YJB6284 (WT) and HBO-1 knockout strain 082-23 (KO) are grown for 22 hours with 100 uM hemin in defined minimal media. Using the column and conditions presented in FIG. 7 above, the biliverdin elutes at 10.6 min and is detected only in the WT strain. Hemin elution at 16 min is not significantly different between the samples. This indicates that HB01 is necessary for biliverdin production (FIG. 8).

EXAMPLE 7

The Regulation of C. albicans Heme Oxygenase By Mammalian Hemoglobin

The regulation of C. albicans heme oxygenase by mammalian hemoglobin reveals a novel adaptation of this fungus to its host environment that has not been described previously for a pathogen. CaHMX1 transcription is rapidly regulated by Hb through its cell surface receptor (Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118) by a mechanism that is distinct from and additive with induction by iron deficiency. These two modes of regulation for the CaHMX1 gene are clearly distinguishable in their time dependence. Induction by Hb occurs within minutes, characteristic of a receptor-mediated response, whereas induction of CaHMX1 by iron requires several hours. Induction by Hb is also distinguishable from the slow induction of CaHMX1 by exogenous hemin. The above-described Examples demonstrate that CaHMX1 encodes a functional heme oxygenase enzyme and that the product of the reaction is exclusively the α-isomer of biliverdin. Heme oxygenases have been identified in several microorganisms and are clearly important for scavenging of iron from heme proteins, but the present invention provides the first evidence that this gene can be regulated in a pathogen by a specific host protein Exclusive production of the α-isomer of biliverdin and loss of this activity following disruption of the gene confirms that CaHMX1 encodes a functional heme oxygenase. Regiospecific cleavage of the α-bridge is a hallmark of mammalian heme oxygenases (Abraham, N. G. et al. (1988) "THE PHYSIOLOGICAL SIGNIFICANCE OF HEME OXYGENASE," Int. J. Biochem. 20:543-558; Maines, M. D. (1988) "HEME OXYGENASE: FUNCTION, MULTIPLICITY, REGULATORY MECHANISMS, AND CLINICAL APPLICATIONS," FASEB J. 2:2557-2568; Schacter, B. A. (1988) "HEME CATABOLISM BY HEME OXYGENASE: PHYSIOLOGY, REGULATION, AND MECHANISM OF ACTION," Semin. Hematol. 25:349-369). The mechanism for heme binding to human heme oxygenase has been defined from the crystal structure (Schuller, D. J. et al. (1999) "CRYSTAL STRUCTURE OF HUMAN HEME OXYGENASE-1," Nat. Struct. Biol. 6:860-867). The heme is orientated with the α meso-edge coordinated with specific internal heme contact residues and the distal γ edge, containing the propionic acids, oriented away from the α cleavage site. The result of this positioning is the exclusive production of the α mesoisomer of biliverdin. The residues that comprise the heme oxygenase signature are all appropriately positioned in the C. albicans enzyme, consistent with the observed isomeric specificity of heme cleavage in C. albicans (FIG. 9).

The existence of heme oxygenase enzymes in microorganisms that spend either part or all of their life cycles in contact with mammalian hosts has only been described recently (e.g. Schmitt, M. P. (1997) "UTILIZATION OF HOST IRON SOURCES BY CORYNEBACTERIUM DIPHTHERIAE: IDENTIFICATION OF A GENE WHOSE PRODUCT IS HOMOLOGOUS TO EUKARYOTIC HEME OXYGENASES AND IS REQUIRED FOR ACQUISITION OF IRON FROM HEME AND HEMOGLOBIN," J. Bacteriol. 179:838-845). However, the ability to utilize heme as a nutritional iron source has been documented extensively (Stojiljkovic, I. et al. (2002) "PROCESSING OF HEME AND HEME-CONTAINING PROTEINS BY BACTERIA," DNA Cell Biol. 21:281-295). In free-living microbes, iron deficiency is a stimulus that induces the microbial genes necessary for recycling of iron from heme (Genco, C. A. et al. (2001) "EMERGING STRATEGIES IN MICROBIAL HAEM CAPTURE," Mol. Microbiol. 39:1-11). On the other hand, C. albicans possesses a Hb receptor (Pendrak, M. L. et al. (2000) "STRUCTURAL REQUIREMENTS FOR HEMOGLOBIN TO INDUCE FIBRONECTIN RECEPTOR EXPRESSION IN CANDIDA ALBICANS," Biochemistry 39:16110-16118) that rapidly couples Hb exposure to intracellular signaling and modulates expression of a number of genes. However, stimulation of CaHMX1 transcription by Hb also occurs under iron sufficiency such as the yeast may encounter in human tissues during advanced disseminated infections. Because Hb is an abundant iron source in a mammalian host, this response may represent an adaptation of CaHMX1 gene regulation to facilitate iron acquisition from its host. Therefore, CaHMX1 may have other functions in addition to utilization of heme and Hb as nutritional iron sources (Santos, R. et al. (2003) "HAEMIN UPTAKE AND USE AS AN IRON SOURCE BY CANDIDA ALBICANS: ROLE OF CAHMX1-ENCODED HAEM OXYGENASE," Microbiology 149:579-588, Weissman, Z. et al. (2002) "DELETION OF THE COPPER TRANSPORTER CACCC2 REVEALS TWO DISTINCT PATHWAYS FOR IRON ACQUISITION IN CANDIDA ALBICANS," Mol. Microbiol. 44, 1551-1560).

The products of the heme oxygenase reaction, CO and biliverdin, are both active biological compounds in mammals (Otterbein, L. E. et al. (2003) "HEME OXYGENASE-1: UNLEASHING THE PROTECTIVE PROPERTIES OF HEME," Trends Immunol. 24(8):449-455). Biliverdin is a potent anti-oxidant (McDonagh, A. F. et al. (1980) "PREPARATION AND PROPERTIES OF CRYSTALLINE BILIVERDIN IX ALPHA. SIMPLE METHODS FOR PREPARING ISOMERICALLY HOMOGENEOUS BILIVERDIN AND [$^{14}$C[BILIVERDIN BY USING 2,3-DICHLORO-5,6-DICYANOBENZOQUINONE," Biochem. J. 189:193-208), and CO has cytoprotective activities in several stress responses (Otterbein, L. E. et al. (2003) "HEME OXYGENASE-1: UNLEASHING THE PROTECTIVE PROPERTIES OF HEME," Trends Immunol. 24(8):449-455, Fujita, T. et al. (2001) "PARADOXICAL RESCUE FROM ISCHEMIC LUNG INJURY BY INHALED CARBON MONOXIDE DRIVEN BY DEREPRESSION OF FIBRINOLYSIS," Nat. Med. 7:598-604). Exogenous hemin added to cultures is largely converted to biliverdin (FIG. 9, Panel B). Biliverdin may serve to protect against oxidative killing by host phagocytes (Hampton, M. B. et al. (1998) "INSIDE THE NEUTROPHIL PHAGOSOME: OXIDANTS, MYELOPEROXIDASE, AND BACTERIAL KILLING," Blood 92:3007-3017). Furthermore, 3 moles of $O_2$ are utilized by heme oxygenase for each mole of heme degraded. This stoichiometry would deplete oxygen from the local environment, reduce the local redox potential, and reduce levels of reactive oxygen species (Otterbein, L. E. et al. (2003) "HEME OXYGENASE-1: UNLEASHING THE PROTECTIVE PROPERTIES OF HEME," Trends Immunol. 24(8):449-455). CO also has potent anti-inflammatory effects on monocytes and macrophages (Otterbein, L. E. et al. (2003) "HEME OXYGENASE-1: UNLEASHING THE PROTECTIVE PROPERTIES OF HEME," Trends Immunol. 24(8):449-455), which could be advantageous to fungal survival in a disseminated infection The only fungal heme oxygenase ortholog that has been described is the *S. cerevisiae* Hmx1p (Reggiori, F. et al. (2001) "SORTING OF PROTEINS INTO MULTIVESICULAR BODIES: UBIQUITIN-DEPENDENT AND -INDEPENDENT TARGETING," EMBO J. 20:5176-5186; Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278:36582-36587). A HMX1 deletion alters iron availability from internal heme pools during iron deficiency (Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278: 36582-36587). Because hemin is transported only very inefficiently in *S. cerevisiae* (Protchenko, O. et al. (2003) "REGULATION OF INTRACELLULAR HEME LEVELS BY HMX1, A HOMOLOGUE OF HEME OXYGENASE, IN *SACCHAROMYCES CEREVISIAE*," J. Biol. Chem. 278:36582-36587), Hmx1p activity in this fungus may be limited to the mobilization of internal iron stores. In support of this, Hb cannot be used as an iron source by *S. cerevisiae*, Hb signaling does not occur in *S. cerevisiae* (Rodrigues, R. G. et al. (1998) "HEMOGLOBIN DIFFERENTIALLY INDUCES BINDING OF *CANDIDA, TRICHOSPORON*, AND *SACCHAROMYCES* SPECIES TO FIBRONECTIN," J. Infect. Dis. 178:497-502), and a true heme oxygenase activity could not be demonstrated for Hmx1p (Auclair, K. et al. (2003) "CLONING AND EXPRESSION OF A HEME BINDING PROTEIN FROM THE GENOME OF *SACCHAROMYCES CEREVISIAE*," Protein Expression Purif. 28:340-349). Thus, the regulation of heme oxygenase identified herein for *C. albicans* is not conserved in a fungus that lives independent of a mammalian host. Interestingly, hemin uptake by *C. albicans* is much more robust (Santos, R. et al. (2003) "HAEMIN UPTAKE AND USE AS AN IRON SOURCE BY *CANDIDA ALBICANS*: ROLE OF CAHMX1-ENCODED HAEM OXYGENASE," Microbiology 149:579-588), suggesting evolution not only in the pathway for heme catabolism but also for acquisition of heme from exogenous heme proteins One aspect of the present invention relates to the identification of four potential Hap1p consensus sites in the CaHMX1 promoter (see FIG. 2, Panel D). An increase in hemin catabolism would be a logical step to increase iron availability under iron deprivation. This would result in an increase in CaHMX1 transcription mediated presumably through a HapI-heme complex. However, exogenous hemin was not a robust inducer of transcription either during log phase or early stationary phase growth. Surprisingly, exogenous hemin inhibited CaHMX1 transcription when stimulated by either exogenous Hb or iron deficiency (FIG. 3, Panel B). Whether this results from intracellular transport of hemin or from cell surface binding remains to be determined. These results imply that extracellular release of heme does not mediate the observed regulation of CaHMX1 by Hb but also suggest *C. albicans* has evolved to limit its acquisition of iron from Hb when it is exposed to exogenous hemin. This may prevent accumulation of toxic levels of iron.

CaHMX1 is one of several Hb-regulated genes in *C. albicans*. Exposure to Hb may be enhanced during invasive infection and may be exacerbated by *C. albicans* hemolysins (Luo, G. et al. (2001) "*CANDIDA* SPECIES EXHIBIT DIFFERENTIAL IN VITRO HEMOLYTIC ACTIVITIES," J. Clin. Microbiol. 39, 2971-2974; Manns, J. M. et al. (1994) "PRODUCTION OF A HEMOLYTIC FACTOR BY *CANDIDA ALBICANS*," Infect. Immun. 62:5154-5156). Hb signaling may provide information about spatial positioning within the host and proximity to locations where host defenses may be encountered. The response of CaHMX1 transcription is very rapid, suggesting that a rapid signaling pathway is controlled by the as yet undefined Hb receptor. Therefore, CaHmx1p may be a useful target for novel antifungals to regulate growth in the iron-restricted environment of a mammalian host and to limit the ability of *C. albicans* to survive in specific host microenvironments In sum, *Candida albicans* is an opportunistic pathogen that has adapted uniquely to life in mammalian hosts. One of the host factors recognized by this yeast is hemoglobin, which binds to a specific cell surface receptor. In addition to its regulating the expression of adhesion receptors on the yeast, hemoglobin induces the expression of a *C. albicans* heme oxygenase (CaHmx1p). Hemoglobin transcriptionally induces the CaHMX1 gene independently of the presence of inorganic iron in the medium. A *Renilla* luciferase reporter driven by the CaHMX1 promoter demonstrated rapid activation of transcription by hemoglobin and (cobalt protoporphyrin IX) globin but not by apoglobin or other proteins. In contrast, iron deficiency or exogenous hemin did not activate the reporter until after 3 hours, suggesting that induction of the promoter by hemoglobin is mediated by receptor signaling rather than heme or iron flux into the cell. As observed following disruption of the *Saccharomyces cerevisiae* ortholog, HMX1, a CaHMX1 null mutant was unable to grow under iron restriction. This suggests a role for CaHmx1p in inorganic iron acquisition. CaHMX1 encodes a functional heme oxygenase. Exogenous heme or hemoglobin is exclusively metabolized to α-biliverdin. CaHMX1 is required for utilization of these exogenous substrates, indicating that *C. albicans* heme oxygenase confers a nutritional advantage for growth in mammalian hosts.

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for producing biliverdin, wherein said method comprises the steps of:
   (A) culturing a microorganism in the presence of a heme compound, wherein said microorganism is a *Candida* yeast selected from the group consisting of *Candida albicans* deposited under number ATCC (MYA-2876) and mutants thereof, and said microorganism possesses a heme oxygenase activity sufficient to convert heme into biliverdin; and
   (B) recovering the produced biliverdin.

2. The method of claim 1, wherein said microorganism substantially lacks a biliverdin reductase activity.

3. The method of claim 1, wherein said microorganism has been modified to enhance said heme oxygenase activity.

4. The method of claim 1, wherein said *Candida* yeast is *Candida albicans*.

5. The method of claim 1, wherein said produced biliverdin is α-biliverdin.

6. A method for producing biliverdin, wherein said method comprises the steps of:

(A) culturing a microorganism in the presence of a heme compound, wherein said microorganism is *Candida albicans* selected from the group consisting of *Candida albicans* deposited under number ATCC (MYA-2876) and mutants thereof, and said microorganism possesses a heme oxygenase activity sufficient to convert heme into biliverdin; and
   (B) recovering the produced biliverdin.

7. The method of claim 6, wherein said microorganism substantially lacks a biliverdin reductase activity.

8. The method of claim 6, wherein said microorganism has been modified to enhance said heme oxygenase activity.

9. The method of claim 6, wherein said produced biliverdin is α-biliverdin.

10. The method of claim 1, wherein the heme compound is hemoglobin.

11. The method of claim 6, wherein the heme compound is hemoglobin.

\* \* \* \* \*

SEQUENCE LISTING

<160> NUMBER OF SEQ ID NOS: 11

<210> SEQ ID NO 1
<211> LENGTH: 18
<212> TYPE: DNA
<213> ORGANISM: Candida albicans

<400> SEQUENCE: 1
cacacgcaca cggaagaa                                               18

<210> SEQ ID NO 2
<211> LENGTH: 79
<212> TYPE: DNA
<213> ORGANISM: Candida albicans

<400> SEQUENCE: 2
ggctaataga ataaatcttg aaaccagatc tttgcacgat agagcagaca agacagttag    60
ttttcccagt cacgacgtt                                              79

<210> SEQ ID NO 3
<211> LENGTH: 73
<212> TYPE: DNA
<213> ORGANISM: Candida albicans

<400> SEQUENCE: 3
gtgacaaacc atctctttgt gggtacatac cagtagcttt gaggaccgac gattgtggaa    60
ttgtgacgcg ata                                                    73

<210> SEQ ID NO 4
<211> LENGTH: 28
<212> TYPE: DNA
<213> ORGANISM: Candida albicans

<400> SEQUENCE: 4
ctgcagattg tatgtgtaat gatatatg                                    28

<210> SEQ ID NO 5
<211> LENGTH: 20
<212> TYPE: DNA
<213> ORGANISM: Candida albicans

<400> SEQUENCE: 5
ccagctaata catcgatggc                                             20

<210> SEQ ID NO 6
<211> LENGTH: 18
<212> TYPE: DNA
<213> ORGANISM: Artificial
<220> FEATURE:
<223> OTHER INFORMATION: artificial primer

<400> SEQUENCE: 6
aatctagagc tcctcctc                                               18

-continued

<210> SEQ ID NO 7
<211> LENGTH: 18
<212> TYPE: DNA
<213> ORGANISM: Artificial
<220> FEATURE:
<223> OTHER INFORMATION: artificial primer

<400> SEQUENCE: 7
aatctagagc tctcctgg                                                      18

<210> SEQ ID NO 8
<211> LENGTH: 18
<212> TYPE: DNA
<213> ORGANISM: Artificial
<220> FEATURE:
<223> OTHER INFORMATION: artificial primer

<400> SEQUENCE: 8
aatctagagc tccagcag                                                      18

<210> SEQ ID NO 9
<211> LENGTH: 18
<212> TYPE: DNA
<213> ORGANISM: Artificial
<220> FEATURE:
<223> OTHER INFORMATION: artificial primer

<400> SEQUENCE: 9
cacacgcaca cggaagaa                                                      18

<210> SEQ ID NO 10
<211> LENGTH: 291
<212> TYPE: PRT
<213> ORGANISM: Candida albicans

<400> SEQUENCE: 10

Met Gln Tyr Lys Ser Ser Gly Ala Thr Ser Lys Leu Ser Gln Val Glu
1               5                   10                  15

Ile Ile Pro Ala Lys Thr Asp Val Gly Ala Leu Ala Asn Arg Ile Asn
            20                  25                  30

Leu Glu Thr Arg Ser Leu His Asp Arg Ala Asp Lys Thr Val Thr Leu
        35                  40                  45

Lys Phe Ala Leu Ala Leu Arg Asn Tyr Lys Val Tyr Arg Gln Gly Leu
    50                  55                  60

Gln Ala Phe Tyr His Val Phe Ala Ser Ile Glu Lys Ala Leu Tyr Arg
65                  70                  75                  80

Gln Leu Glu Lys Lys Asp Glu Trp Ser Glu Met Leu Glu Gln Val Trp
                85                  90                  95

Lys Pro Glu Ile Ala Arg Ala Gly Lys Ala Glu Gln Asp Leu Leu Phe
            100                 105                 110

Phe Tyr Asp Asp Asn Lys Glu Lys Phe Ile Lys Pro Ile Met Pro Ala
        115                 120                 125

Gln Ile Glu Phe Cys Lys His Ile Leu Glu Val Thr Glu Glu Lys Pro
    130                 135                 140

Tyr Leu Leu Phe Ala Tyr Leu His Val Met Tyr Leu Ala Leu Phe Ala
145                 150                 155                 160

Gly Gly Arg Ile Met Arg Ser Ser Val Leu Lys Ala Thr Gly Met Tyr
                165                 170                 175

Pro Gln Arg Asp Gly Leu Ser His Asp Asp Val Val Arg Met Gly Thr

```
                180                 185                 190
Asn Phe Phe Thr Phe Asp Val Pro Asp Glu Asp Leu Leu Arg Leu Thr
            195                 200                 205
Tyr Lys Arg Asp Tyr Glu Leu Val Thr Arg Asn Gly Leu Thr Glu Glu
        210                 215                 220
Gln Lys Leu Glu Ile Ile Glu Glu Ser Lys Tyr Ile Phe Glu His Asp
225                 230                 235                 240
Val Lys Cys Val Ala Glu Leu Glu Lys His Asn Met Asp Lys Leu Ser
                245                 250                 255
Gly Thr Trp Thr Tyr Phe Leu Val Thr Arg Gly Tyr Tyr Ala Ala Leu
            260                 265                 270
Val Leu Phe Ser Leu Leu Ala Leu Ile Tyr Leu Arg Arg Val Val Asn
        275                 280                 285
Lys Leu Thr
    290

<210> SEQ ID NO 11
<211> LENGTH: 260
<212> TYPE: PRT
<213> ORGANISM: Homo sapiens

<400> SEQUENCE: 11

Met Glu Arg Pro Gln Pro Asp Ser Met Pro Gln Asp Leu Ser Glu Ala
1               5                   10                  15
Leu Lys Glu Ala Thr Lys Glu Val His Thr Gln Ala Glu Asn Ala Glu
            20                  25                  30
Phe Met Arg Asn Phe Gln Lys Gly Gln Val Thr Arg Asp Gly Phe Lys
        35                  40                  45
Leu Val Met Ala Ser Leu Tyr His Ile Tyr Val Ala Leu Glu Glu Glu
    50                  55                  60
Ile Glu Arg Asn Lys Glu Ser Pro Val Phe Ala Pro Val Tyr Phe Pro
65                  70                  75                  80
Glu Glu Leu His Arg Lys Ala Ala Leu Glu Gln Asp Leu Ala Phe Trp
                85                  90                  95
Tyr Gly Pro Arg Trp Gln Glu Val Ile Pro Tyr Thr Pro Ala Met Gln
            100                 105                 110
Arg Tyr Val Lys Arg Leu His Glu Val Gly Arg Thr Glu Pro Glu Leu
        115                 120                 125
Leu Val Ala His Ala Tyr Thr Arg Tyr Leu Gly Asp Leu Ser Gly Gly
    130                 135                 140
Gln Val Leu Lys Lys Ile Ala Gln Lys Ala Leu Asp Leu Pro Ser Ser
145                 150                 155                 160
Gly Glu Gly Leu Ala Phe Phe Thr Phe Pro Asn Ile Ala Ser Ala Thr
                165                 170                 175
Lys Phe Lys Gln Leu Tyr Arg Ser Arg Met Asn Ser Leu Glu Met Thr
            180                 185                 190
Pro Ala Val Arg Gln Arg Val Ile Glu Glu Ala Lys Thr Ala Phe Leu
        195                 200                 205
Leu Asn Ile Gln Leu Phe Glu Glu Leu Gln Glu Leu Leu Thr His Asp
    210                 215                 220
Thr Lys Asp Gln Ser Pro Ser Arg Ala Pro Gly Leu Arg Gln Arg Ala
225                 230                 235                 240
```

-continued

```
Ser Asn Lys Val Gln Asp Ser Ala Pro Val Glu Thr Pro Arg Gly Lys
                245                 250                 255

Pro Pro Leu Asn
            260
```